(12) United States Patent
Brinkman et al.

(10) Patent No.: US 9,554,835 B2
(45) Date of Patent: Jan. 31, 2017

(54) SURGICAL IMPLANT SYSTEM AND METHOD

(71) Applicant: Warsaw Orthopedic, Inc., Warsaw, IN (US)

(72) Inventors: Jennifer G. Brinkman, Memphis, TN (US); Nicholas M. Benson, Cordova, TN (US); David W. Harwood, Memphis, TN (US); Larry Thomas McBride, Jr., Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 140 days.

(21) Appl. No.: 13/827,485

(22) Filed: Mar. 14, 2013

(65) Prior Publication Data

US 2014/0277166 A1    Sep. 18, 2014

(51) Int. Cl.
*A61B 17/70*    (2006.01)

(52) U.S. Cl.
CPC ........ *A61B 17/7085* (2013.01); *A61B 17/7083* (2013.01); *A61B 17/7086* (2013.01); *A61B 17/7088* (2013.01); *A61B 17/7004* (2013.01)

(58) Field of Classification Search
CPC ............ A61B 17/7083; A61B 17/7085; A61B 17/7086; A61B 17/7088; A61B 17/7089
See application file for complete search history.

(56) References Cited

U.S. PATENT DOCUMENTS

| | | | |
|---|---|---|---|
| 6,755,338 B2 | 6/2004 | Hahnen et al. | |
| 7,371,239 B2 | 5/2008 | Dec et al. | |
| 7,462,182 B2 | 12/2008 | Lim | |
| 7,476,240 B2 | 1/2009 | Raymond et al. | |
| 7,481,813 B1 | 1/2009 | Purcell | |
| 7,520,879 B2 | 4/2009 | Justis et al. | |
| 7,563,274 B2 | 7/2009 | Justis et al. | |
| 7,572,276 B2 | 8/2009 | Lim et al. | |
| 7,597,694 B2 | 10/2009 | Lim et al. | |
| 7,648,507 B2 | 1/2010 | Techiera et al. | |
| 7,686,809 B2 | 3/2010 | Triplett et al. | |
| 7,695,475 B2 | 4/2010 | Justis et al. | |
| 7,758,584 B2 | 7/2010 | Bankoski et al. | |
| 7,871,424 B2 | 1/2011 | Abdelgany | |

(Continued)

FOREIGN PATENT DOCUMENTS

| | | |
|---|---|---|
| DE | 10032126 A1 | 1/2002 |
| EP | 1916954 A2 | 5/2008 |

(Continued)

OTHER PUBLICATIONS

International Search Report and Written Opinion for PCT/US2014/025338, the counterpart application mailed on Jul. 11, 2014.

*Primary Examiner* — Eduardo C Robert
*Assistant Examiner* — Julianna N Harvey

(57) ABSTRACT

A surgical instrument comprises a body. A first member extends between a first end and a second end. A second member extends between a first end connected with the body and a second end. A third member is connected to the first end of the first member and the body to relatively axially translate the second ends. The third member includes a latch and a lock engageable with the latch. The latch is disposable in a locking orientation and a non-locking orientation. Systems and methods of use are disclosed.

20 Claims, 19 Drawing Sheets

(56) References Cited

U.S. PATENT DOCUMENTS

| | | |
|---|---|---|
| 7,914,558 B2 | 3/2011 | Landry et al. |
| 7,998,144 B2 | 8/2011 | Schumacher et al. |
| 8,025,682 B2 | 9/2011 | Mahoney et al. |
| 8,043,343 B2 | 10/2011 | Miller et al. |
| 8,075,592 B2 | 12/2011 | Landry et al. |
| 8,100,951 B2 | 1/2012 | Justis et al. |
| 8,142,437 B2 | 3/2012 | McLean et al. |
| 8,167,887 B2 | 5/2012 | McLean |
| 8,192,439 B2 | 6/2012 | Songer et al. |
| 8,206,394 B2 | 6/2012 | Stad et al. |
| 8,226,656 B2 | 7/2012 | McBride |
| 8,246,624 B2 | 8/2012 | Forton et al. |
| 8,308,728 B2 | 11/2012 | Iott et al. |
| 8,348,954 B2 | 1/2013 | Carls et al. |
| 8,366,714 B2 | 2/2013 | Jones et al. |
| 8,460,301 B2 | 6/2013 | Fiorella |
| 2005/0192589 A1 | 9/2005 | Raymond et al. |
| 2005/0228392 A1 | 10/2005 | Keyer et al. |
| 2007/0078460 A1 | 4/2007 | Frigg et al. |
| 2007/0123904 A1 | 5/2007 | Stad et al. |
| 2007/0213714 A1 | 9/2007 | Justis et al. |
| 2008/0121234 A1 | 5/2008 | Ho et al. |
| 2008/0269764 A1 | 10/2008 | Blain et al. |
| 2008/0269805 A1 | 10/2008 | Dekutoski et al. |
| 2008/0312703 A1 | 12/2008 | Hestad et al. |
| 2009/0198281 A1 | 8/2009 | Rice et al. |
| 2010/0036443 A1 | 2/2010 | Hutton et al. |
| 2010/0249856 A1 | 9/2010 | Iott et al. |
| 2011/0077690 A1 | 3/2011 | Shin et al. |
| 2011/0093014 A1 | 4/2011 | Davis et al. |
| 2011/0166610 A1 | 7/2011 | Altarac et al. |
| 2011/0184464 A1 | 7/2011 | Fiorella |
| 2011/0196426 A1 | 8/2011 | Peukert et al. |
| 2011/0202096 A1 | 8/2011 | White et al. |
| 2011/0313470 A1* | 12/2011 | McLean ............ A61B 17/7011 606/305 |
| 2012/0029580 A1 | 2/2012 | Solitario, Jr. |
| 2012/0053643 A1 | 3/2012 | Harper |
| 2012/0271355 A1 | 10/2012 | Steele et al. |
| 2013/0018423 A1 | 1/2013 | Stad et al. |

FOREIGN PATENT DOCUMENTS

| | | |
|---|---|---|
| EP | 2111809 A2 | 10/2009 |
| KR | 2008059920 A1 | 7/2008 |
| KR | 2009072327 A1 | 7/2009 |
| KR | 1001539 A1 | 12/2010 |
| KR | 2011029988 A1 | 3/2011 |

\* cited by examiner

US 9,554,835 B2

SURGICAL IMPLANT SYSTEM AND METHOD

TECHNICAL FIELD

The present disclosure generally relates to medical devices for the treatment of musculoskeletal disorders, and more particularly to a surgical implant system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. This disclosure describes an improvement over these prior art technologies.

SUMMARY

In one embodiment, a surgical instrument is provided. The surgical instrument comprises a body. A first member extends between a first end and a second end. A second member extends between a first end connected with the body and a second end. A third member is connected to the first end of the first member and the body to relatively axially translate the second ends. The third member includes a latch and a lock engageable with the latch. The latch is disposable in a locking orientation such that the second ends engage a spinal construct and rotatable to a non-locking orientation such that the lock disengages the latch and the latch is biased relative to the body such that the second ends are disposed to disengage the spinal construct.

BRIEF DESCRIPTION OF THE DRAWINGS

The present disclosure will become more readily apparent from the specific description accompanied by the following drawings, in which.

DETAILED DESCRIPTION

Figure 1:
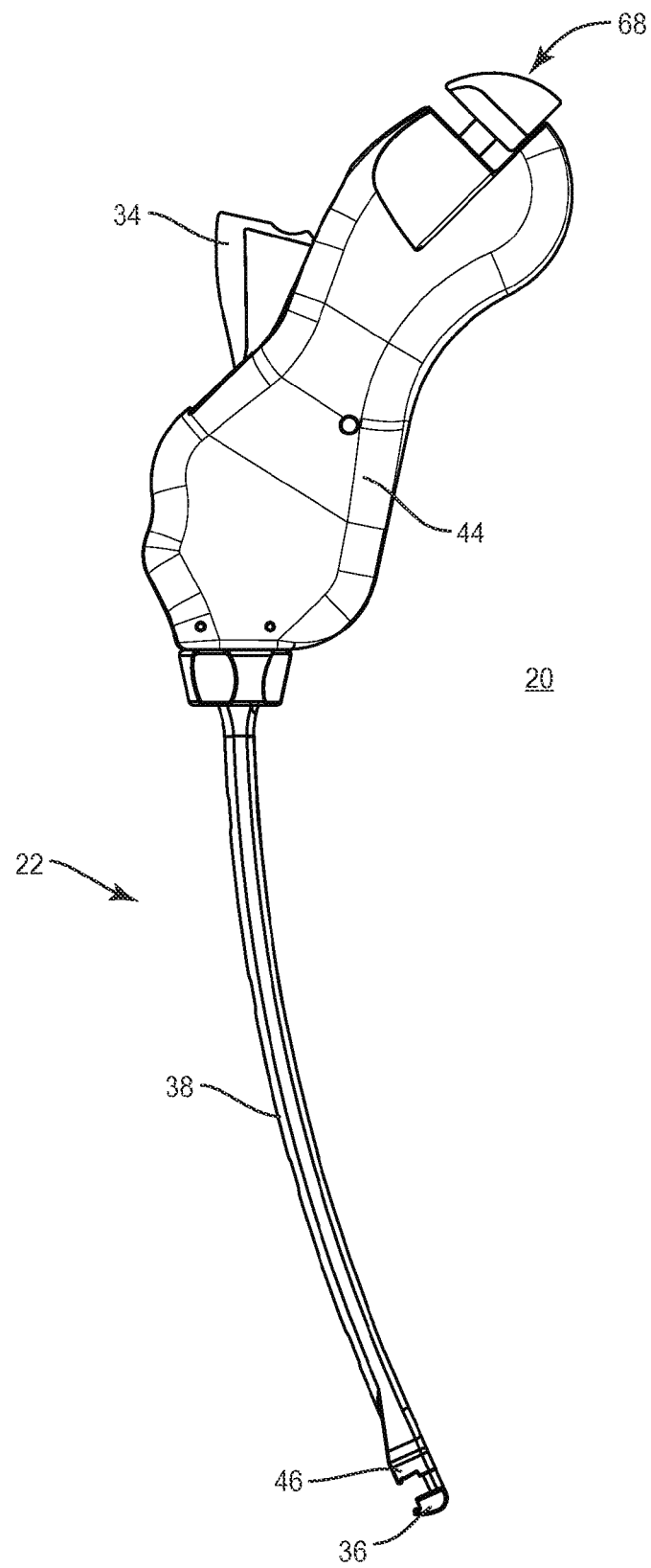
FIG. 1 is a side view of components of one embodiment of a surgical implant system in accordance with the principles of the present disclosure.

The exemplary embodiments of the surgical implant system and related methods of use disclosed are discussed in terms of medical devices for the treatment of musculoskeletal disorders and more particularly, in terms of a surgical implant system for implant delivery to a surgical site and a method for treating a spine.

In one embodiment, the surgical implant system is employed with a method that includes inserting a rod through the same stab incision in which a pedicle screw was placed percutaneously. In one embodiment, the system includes a surgical instrument, such as, for example, a rod inserter. In one embodiment, the surgical instrument clamps an implant, such as, for example, a longitudinal rod, by pulling a flexible shaft through a cannulated main body of the rod inserter. In one embodiment, the surgical instrument includes an outer sleeve having a T-slot cross section and a flexible inner shaft having one or a plurality of T-shaped beads, for example, four beads, that movably retain the inner shaft with the outer sleeve. For example, the beads are assembled with the outer sleeve by passing the beads through openings of the outer sleeve. The beads are retained with the outer sleeve when a latch, described herein, is closed because a collet, described herein, is drawn through the T-slot and the beads are not visible in the openings.

In one embodiment, the system includes a surgical instrument, such as, for example, a rod inserter that can be used with extended tab screws or other extenders with an extended rod guide. In one embodiment, the rod is initially placed, inclined relative to the extenders, in a stab incision in which a pedicle screw has been placed percutaneously. The rod is moved to the surgical site such that the rod is inclined relative to the extenders. As the rod is moved closer to a saddle of a pedicle screw, the rod is rotated to a position within a first and at least a second pedicle screw. Once in place, the rod is released. In one embodiment, the inserter shaft remains outside the screw extenders. In one embodiment, the shaft resides between two extensions attached to a pedicle screw or within a feature of an extender. In one embodiment, the geometry of the shaft allows the mechanism to have three functional components and a handle. In some embodiments, the method includes inserting a rod percutaneously without the need to make an additional incision.

In one embodiment, the surgical instrument, such as, for example, a rod inserter, includes a tension adjustment mechanism using a hex socket style adjustment. In one embodiment, the tension adjustment mechanism is externally controlled. In one embodiment, inserting a hex key into the socket turns a shaft threaded with the rod inserter to increase or decrease tension of the clamp. In one embodiment, the shaft is attached to a translation sleeve and is allowed to rotate in relation to the translation sleeve, which translates axially. In one embodiment, the rod inserter includes a leaf spring detent so that a user turns the shaft to set clamp force without any additional step being required. In one embodiment, the detent holds the shaft in place reducing the steps required to adjust the tension.

In one embodiment, the surgical instrument includes a rod inserter having an outer sleeve configured to fit between tab extenders and a clamp at its distal end configured not to fit between tab extenders. This configuration resists and/or prevents having a cone end of a spinal rod inside the tulip head of a bone screw. In one embodiment, the cone of the spinal rod is maintained outside of the tulip head so that the set screw clamps on the outer diameter of the rod to provide maximum grip strength. In one embodiment, the sides of the rod inserter clamps resist and/or prevent the clamp from entering too far into the extender or screw tulip.

In one embodiment, the surgical instrument includes a rod inserter having an ergonomic handle including a latch and a collet release for attachment of a rod to the inserter. In one embodiment, the rod inserter includes a collet at a distal end of the rod inserter. In some embodiments, the rod inserter allows the rod to be inserted through the same stab incision that the pedicle screw and extender were inserted. In one embodiment, the latch and release provide, for example, looser tolerances. In one embodiment, as the collet release is pulled a distance away from the handle, the latch rotates to protrude out of the handle. In one embodiment, applying a force to the latch to cause the latch to protrude further from the handle causes the collet at the distal end of the rod inserter to open and disengage the rod. In one embodiment, to close the collet, a force is applied to the latch in a direction towards the handle. In one embodiment, the rod inserter allows for disassembly and the handle is configured to be ergonomic irrespective of which direction a user is holding the handle. The rod inserter can be rotated, for example, 180 degrees and a user will still be able to grip the handle and manipulate it as required by a particular application.

In one embodiment, the surgical instrument includes a rod inserter having a latch, a collet release, a thumb groove, finger grooves and a collet. From a locking orientation, the collet is drawn such that the latch will pop out to a non-locking orientation. In some embodiments, from the non-locking orientation, the latch can be manually drawn open such that the collet is caused to open wider. A rod is inserted with the collet having the flats facing up. The latch is closed to lock the rod in place and the collet release returns to the locking orientation automatically. In one embodiment, the surgical instrument allows a rod to be inserted through extenders along a path that includes a distal and/or far location from a practitioner and/or a selected starting point of the path, to a proximal and/or near location to the practitioner and/or selected endpoint of the path. In one embodiment, the surgical instrument allows a rod to be inserted through extenders along a path that includes a proximal and/or near location to the practitioner and/or selected starting point of the path, to a distal and/or far location from a practitioner and/or a selected endpoint of the path. The handle can be rotated 180 degrees.

In one embodiment, the collet release is disengageable such that the collet automatically translates, for example, is spring biased to a locked position. In one embodiment, the collet release is rotatable and/or can be pulled for automatic release. In one embodiment, the collet release and the handle have an inclined ramp configuration to facilitate locking and realigning the collet release in a locked position. In one embodiment, the collet release includes a V-shaped groove that mates with a V-shaped wedge of the handle. In one embodiment, the handle is ergonomically designed to be held in a plurality of orientations, for example, to release and tighten a collet supporting a spinal rod in the plurality of orientations. In one embodiment, the handle and an outer sleeve have the same radius. In one embodiment, the handle and the outer sleeve have a continuous curvature. In one embodiment, the handle and an outer sleeve have an offset radius. In one embodiment, the handle has a first radius and the outer sleeve has a second radius, the first radius and the second radius being distinct. In one embodiment, the handle has a first width and the outer sleeve has a second width, the first width and the second width being distinct.

In one embodiment, the rod inserter includes an internal pin that slides while the latch rotates to maintain the collet motion linear. In one embodiment, the rod inserter includes an outer sleeve having threads to aide in tightening of the collet. In one embodiment, the rod inserter includes a collet disposable in a first position to unlock the collet and release a rod. In one embodiment, in the second position, the collet translates, for example, is spring biased out for disassembly.

In one embodiment, the surgical instrument is employed with a surgical method that includes the steps of creating a first incision for disposal of at least one extender and creating an additional incision. In one embodiment, the method includes the step of inserting a spinal rod at a three dimensional angle in space, for example, angular orientations in intersecting planes, from a first extender until the spinal rod reaches a saddle of a screw. In one embodiment, the method includes the step of inserting a spinal rod at an angle, for example, a cephalad-caudal angle and an angle, for example, a medial/lateral angle relative to an extender. In one embodiment, the method includes the step of rotating the handle to push a tip of the spinal rod through the saddle and through to a second screw. In one embodiment, the step of rotating includes inserting and rotating the spinal rod within a coronal plane.

In one embodiment, the surgical instrument is employed with a surgical method that includes the steps of gripping an ergonomic handle of a percutaneous inserter in a selected orientation, and inserting a spinal rod at a three dimensional angle from an extender. In some embodiments, the method includes the step of simultaneously lowering and rotating a spinal rod through to subsequent extenders. In some embodiments, the method includes the step of releasing the spinal rod after insertion with a screw via a release knob and removing the inserter from a patient.

In one embodiment, the surgical instrument is employed with a surgical method for pulling a spinal rod, for example, along a far to near orientation, as described, through at least one extender, which includes the steps of gripping the handle of an inserter prior to insertion of the inserter with a body, the inserter having a spinal rod disposed therewith; inserting a distal tip of the spinal rod inside an extender window and an axis of the spinal rod being disposed at an angle offset from the extender until the spinal rod is below the skin and the fascia; disposing the spinal rod in a medial or lateral orientation to prevent the handle of the inserter from interfering with the extender to create a three dimensional angle; and simultaneously lowering the spinal rod to a first screw head while rotating the spinal rod through to subsequent extenders.

In one embodiment, the surgical instrument is employed with a surgical method for pushing a spinal rod, for example, along a near to far orientation, as described, through at least one extender, which includes the steps of gripping the handle of an inserter prior to insertion of the inserter with a body, the inserter having a spinal rod disposed therewith; and inserting a distal tip of the spinal rod inside an extender window and an axis of the spinal rod being disposed at an angle offset from the extender until the spinal rod is below the skin and the fascia; and simultaneously lowering the spinal rod to a first screw head while rotating the spinal rod through to subsequent extenders. In one embodiment, the method includes the step of removing the spinal rod from the inserter, which includes gripping a release knob of the inserter and rotating the release knob in a clockwise or counterclockwise direction, and/or pulling the release knob. In one embodiment, the method includes the step of removing the spinal rod from the inserter, which includes manipulating a release knob of the inserter and rotating the release knob to release the spinal rod from the inserter.

In one embodiment, one or all of the components of the system are disposable, peel-pack, pre-packed sterile devices used with an implant. One or all of the components of the system may be reusable. The system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical implant system and related methods of employing the surgical implant system in accordance with the principles of the present disclosure. Alternate embodiments are also disclosed. Reference will now be made in detail to the exemplary embodiments of the present disclosure, which are illustrated in the accompanying figures. Turning to FIGS. 1-8, there are illustrated components of a surgical system, such as, for example, a surgical implant system 20 in accordance with the principles of the present disclosure.

The components of system 20 can be fabricated from biologically acceptable materials suitable for medical applications, including metals, synthetic polymers, ceramics and bone material and/or their composites, depending on the particular application and/or preference of a medical practitioner. For example, the components of system 20, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 20 may have material composites, including the above materials, to achieve various desired characteristics such as strength, rigidity, elasticity, compliance, biomechanical performance, durability and radiolucency or imaging preference. The components of system 20, individually or collectively, may also be fabricated from a heterogeneous material such as a combination of two or more of the above-described materials. The components of system 20 may be monolithically formed, integrally connected or include fastening elements and/or instruments, as described herein.

System 20 is employed, for example, with a minimally invasive procedure, including percutaneous techniques, mini-open and open surgical techniques to deliver and introduce an implant, such as, for example, a spinal construct, at a surgical site within a body of a patient, for example, a section of a spine. In some embodiments, system 20 may include and/or deliver and introduce implants such as spinal rods, bone fasteners, connectors, plates and interbody devices. System 20 includes a surgical instrument 22 that is configured for engagement with a spinal construct, such as, for example, a spinal rod 10.

Instrument 22 includes a first member, such as, for example, a flexible inner shaft 24 extending between an end 26 and an end 28. Shaft 24 has a cylindrical cross-section configuration. In some embodiments, shaft 24 may have variously configured cross-sections, such as, for example, round, oval, rectangular, polygonal, irregular and/or tapered. End 26 includes a bead 30 configured for translation within a slot 32 of a latch 34. End 28 includes a clamp, such as, for example, a jaw 36 that is configured for engagement with spinal rod 10. Shaft 24 includes a range of translation between a proximal most position and a distal most position. In some embodiments, shaft 24 can include a socket configured to engage a correspondingly shaped portion of a driving tool (not shown) such that shaft 24 translates relative to sleeve 38 to selectively tension the engagement of jaws 36, 46 with spinal rod 10 to selectively set the clamping force on spinal rod 10.

Instrument 22 includes a second member, such as, for example, an outer sleeve 38. Sleeve 38 extends between an end 40 and an end 42. End 40 includes a threaded outer surface 41 configured for threaded engagement with a rotatable part, such as, for example, a hex nut 51 of a handle body 44 such that sleeve 38 translates relative to handle body 44 to selectively tension the engagement of jaws 36, 46 with spinal rod 10 to selectively set the clamping force on spinal rod 10. End 42 includes a clamp, such as, for example, a jaw 46. Jaws 36, 46 comprise a collet of instrument 22. Relative movement of jaws 36, 46 is facilitated with relative axial translation of shaft 24 and sleeve 38.

Sleeve 38 defines a cavity configured for disposal of a portion of shaft 24. Sleeve 38 has an arcuate curvature, which defines a radius of curvature, extending between ends 40, 42. In one embodiment, the cavity of sleeve 38 has a T-slot cross section for disposal of shaft 24. Shaft 24 includes four T-shaped beads spaced apart along shaft 24 that movably retain shaft 24 with sleeve 38. For example, the beads are assembled with sleeve 38 by passing the beads through openings 48 of sleeve 38. In one embodiment, the beads are retained with sleeve 38 when a latch, described herein, is closed because a collet, described herein, is drawn through the T-slot cavity of sleeve 38 and the beads are not visible in openings 48. In one embodiment, openings 48 provide visualization of shaft 24 and cleaning. In some embodiments, sleeve 38 may have alternate cross section shapes, such as, for example, oval, circular, oblong, triangular, square, polygonal, irregular, uniform, non-uniform, offset, staggered, undulating, arcuate, variable and/or tapered depending on a particular application.

Handle body 44 extends between an end 50 and an end 52. End 50 includes hex nut 51 configured for threaded engagement with end 40. Hex nut 51 is rotatably connected to end 50. Rotation of hex nut 51 causes axial translation of sleeve 38 relative to handle body 44 to selectively tension the engagement of jaws 36, 46 with spinal rod 10 to selectively set the clamping force on spinal rod 10. Handle body 44 has an arcuate curvature, which defines a radius of curvature, extending between ends 50, 52. End 50 defines a cavity 54 configured for disposal of a portion of shaft 24. Handle body 44 includes an outer surface 56 that defines finger grooves 58 and a thumb groove 60. In some embodiments, outer surface 56 may have various surface configurations, such as, for example, rough, threaded, arcuate, undulating, porous, semi-porous, dimpled, polished and/or textured, to enhance gripping of handle body 44.

In one embodiment, handle body 44 is ergonomically designed to be held in a plurality of orientations such that jaws 36, 46 support spinal rod 10 in a plurality of orientations. In some embodiments, the plurality of orientations can include relative angular orientations, parallel, perpendicular, offset and/or include manipulation of the planes of a body, such as, for example, coronal, sagittal and/or transverse. In one embodiment, handle body 44 and sleeve 38 have the same radius. In one embodiment, handle body 44 and sleeve 38 have a continuous curvature. In one embodiment, handle body 44 and sleeve 38 have an offset radius. In one embodiment, handle body 44 has a first radius and sleeve 38 has a second radius, the first radius and the second radius being distinct. In one embodiment, handle body 44 has a first width and sleeve 38 has a second width, the first width and the second width being distinct. In some embodiments, handle body 44 includes an outer surface having a plurality of widths, the widths having an ergonomic configuration to facilitate manipulation thereof.

Handle body 44 defines a cavity configured for disposal of a third member, such as, for example, an actuator, which includes a part, such as, for example, manipulable latch 34 mounted with handle body 44. Latch 34 is resiliently biased for rotation relative to handle body 44 by a biasing member, such as, for example, a torsion spring 64. In some embodiments, the biasing member may include an elastomeric member, clip, leaf spring, coil spring, gravity induced configuration, pneumatic configuration, hydraulic configuration and/or manual lever.

Figure 2:
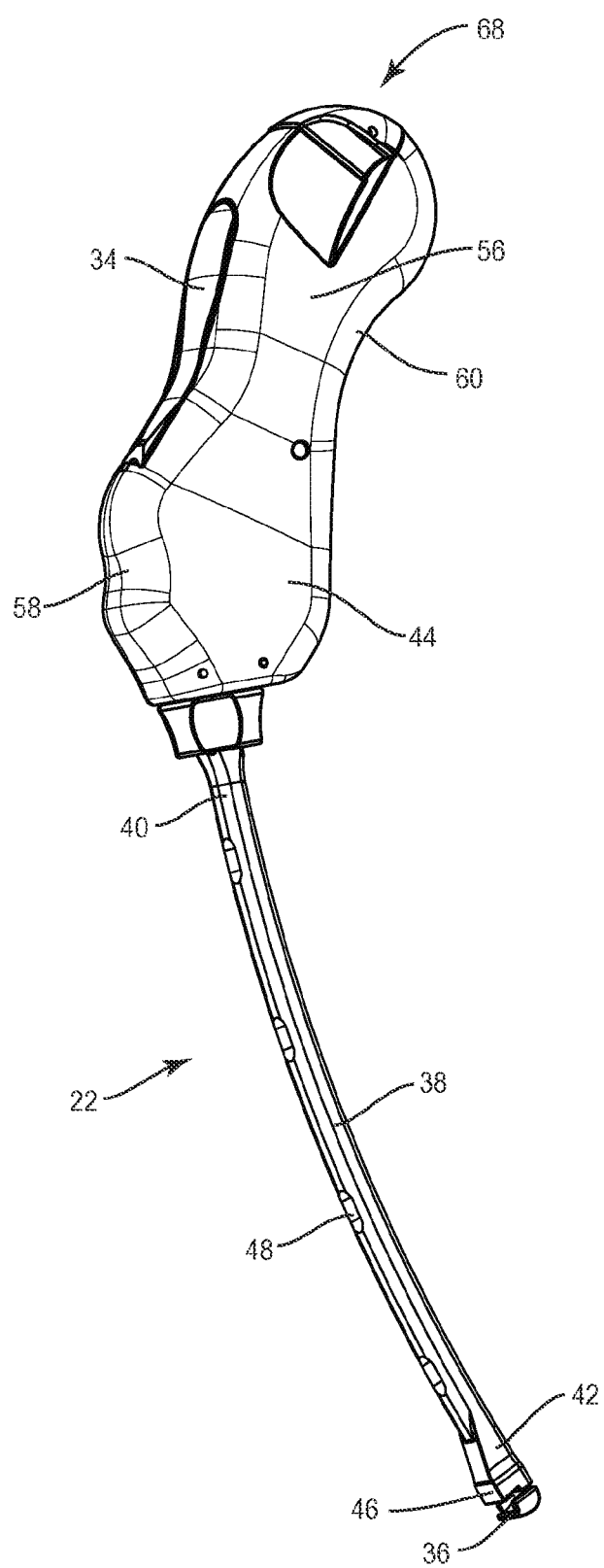
FIG. 2 is a perspective view of the components shown in FIG. 1.
Figure 3:
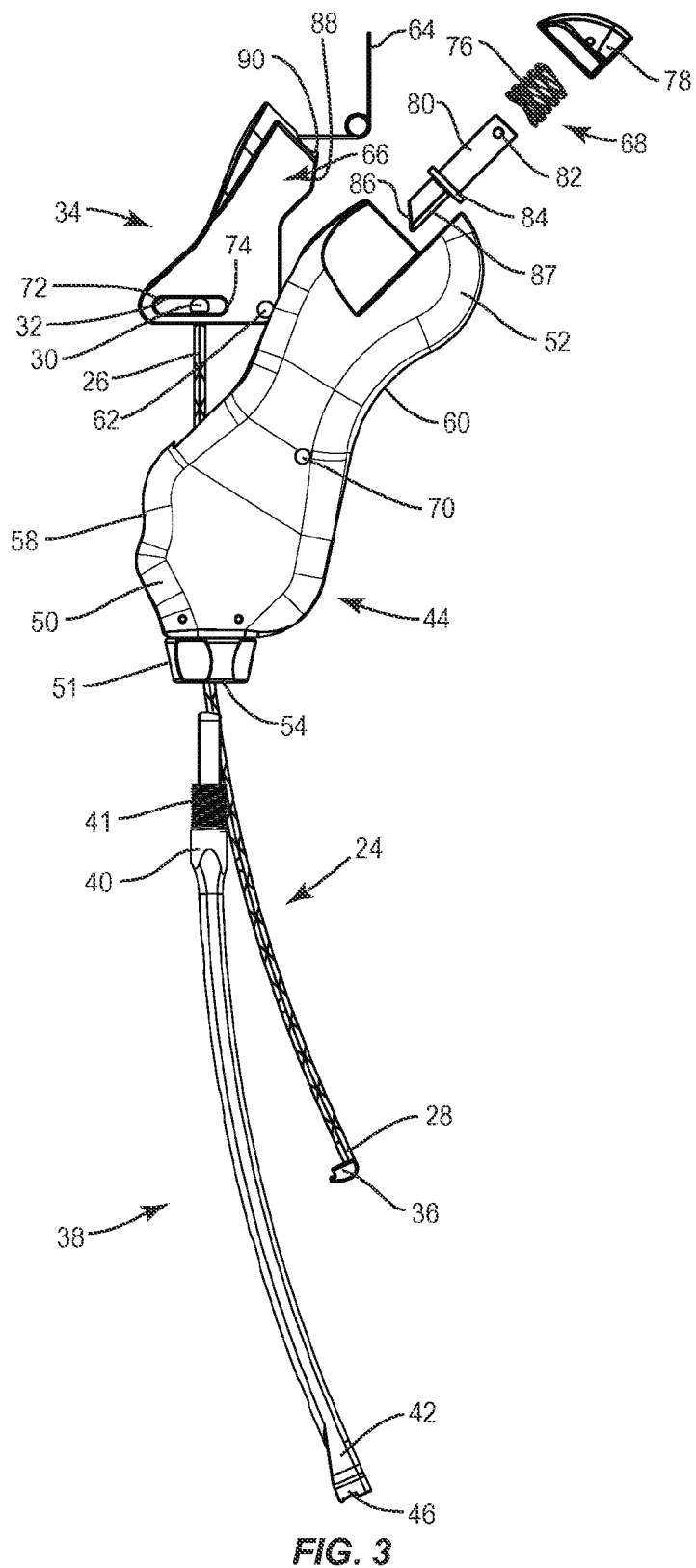
FIG. 3 is a side view of the components shown in FIG. 1 with parts separated.
Figure 6:
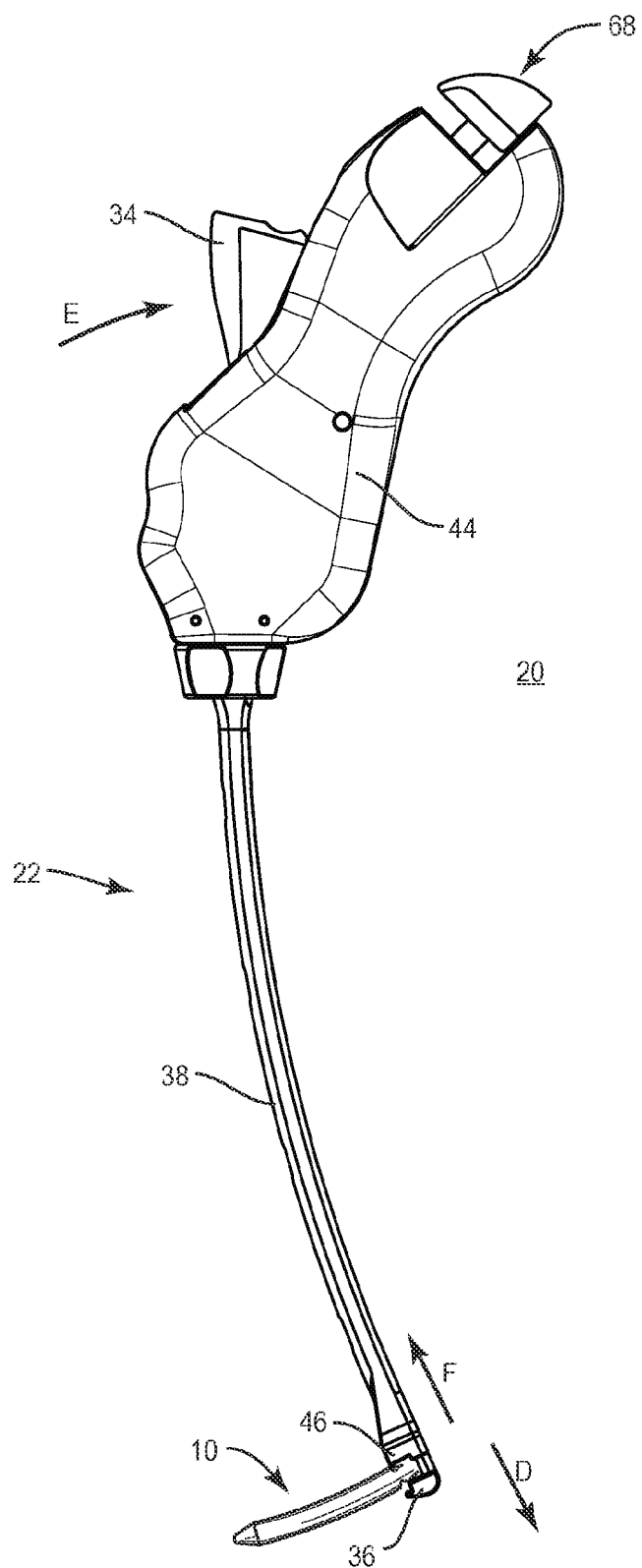
FIG. 6 is a side view of components of one embodiment of a surgical implant system in accordance with the principles of the present disclosure.

Spring 64 is disposed within handle body 44 and rotates latch 34 between a non-locking orientation, as shown in FIG. 1, and a locking orientation, as shown in FIG. 2. Latch 34 is manipulable to the non-locking orientation, as shown in FIG. 6, to release spinal rod 14 from jaws 36, 46. Latch 34 defines a cavity 66 configured for disposal of a locking element, such as, for example, a collet release 68, as described herein. Latch 34 is connected to handle body 44 via a pin 62 at a pivot point 70. In some embodiments, from the non-locking orientation, latch 34 can be manually drawn open such that jaws 36, 46 are caused to open wider.

Latch 34 and shaft 24 are connected such that rotation of latch 34 about pivot point 70 causes axial translation of shaft 24 within and relative to sleeve 38. For example, latch 34 can include slot 32 configured for translation of bead 30 of shaft 24 between movable limits provided by the surface that defines slot 32. Slot 32 extends between a first movable limit, such as, for example, an end 72 and a second movable limit, such as, for example, an end 74 having a uniform thickness therebetween. Bead 30 is translatable between ends 72 and 74.

Collet release 68 is resiliently biased to engage latch 34 via a biasing member, such as, for example, a coil spring 76 disposed within handle body 44. In some embodiments, the biasing member may include an elastomeric member, clip, torsion spring, leaf spring, gravity induced configuration, pneumatic configuration, hydraulic configuration and/or manual lever. Collet release 68 includes a first portion, such as, for example, a release handle 78 and a second portion, such as, for example, a lock 80 extending therefrom. Release handle 78 is connected to lock 80 via a pin 82 and spring 76 is disposed about lock 80.

Figure 5:
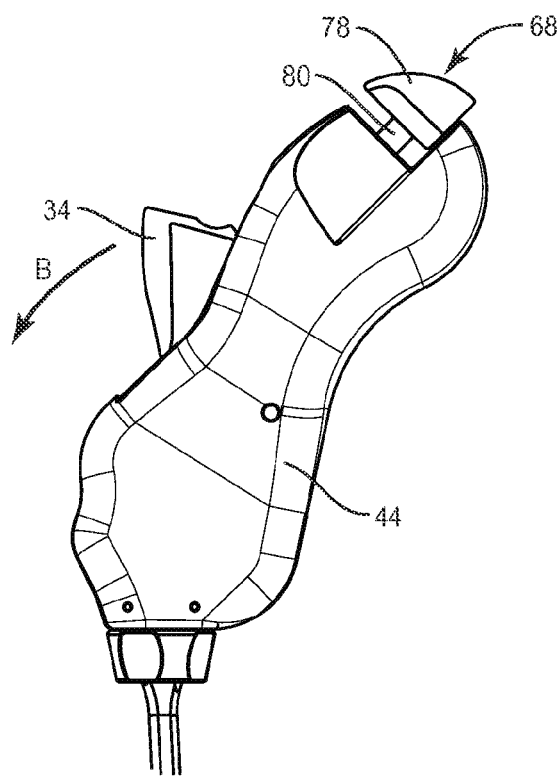
FIG. 5 is a break away view of the components shown in FIG. 2.

Release handle 78 is manipulable axially to a non-locking orientation to release latch 34 for rotation to the non-locking orientation, as shown in FIG. 5, and such that spring 76 is compressed between release handle 78 and a flange 84 of lock 80. In the non-locking orientation, spring 76 is configured to bias lock 80 into a locking orientation with latch 34. Lock 80 includes an inclined ramp 86 configured for engagement with a ledge 88 of latch 34. Lock 80 includes a surface 87 disposed adjacent inclined ramp 86 configured for engagement with a ledge 90 of latch 34 to retain latch 34 in a locking orientation. Surface 87 and ledge 90 are engageable between the locking and non-locking orientations of collet release 68 to dispose latch 34 between the locking and non-locking orientations of latch 34, as described herein.

For example, collet release 68 is movable between a locking orientation, as shown in FIG. 2, such that surface 87 is fixed with ledge 90 so that lock 80 prevents latch 34 from rotating relative to handle body 44 and a non-locking orientation, as shown in FIG. 5, such that ledge 90 is released from surface 87 and latch 34 is rotatable via spring 64. In some embodiments, latch 34 can be angled between 10 and 80 degrees relative to shaft 24 and sleeve 38 such that in the locking orientation, latch 34 is substantially non-parallel and non-perpendicular with an extender, as described herein.

Figure 4:
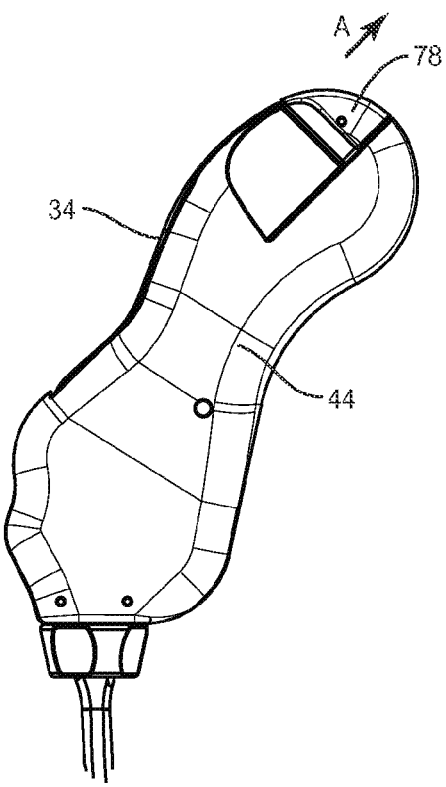
FIG. 4 is a break away view of the components shown in FIG. 2.
Figure 7:
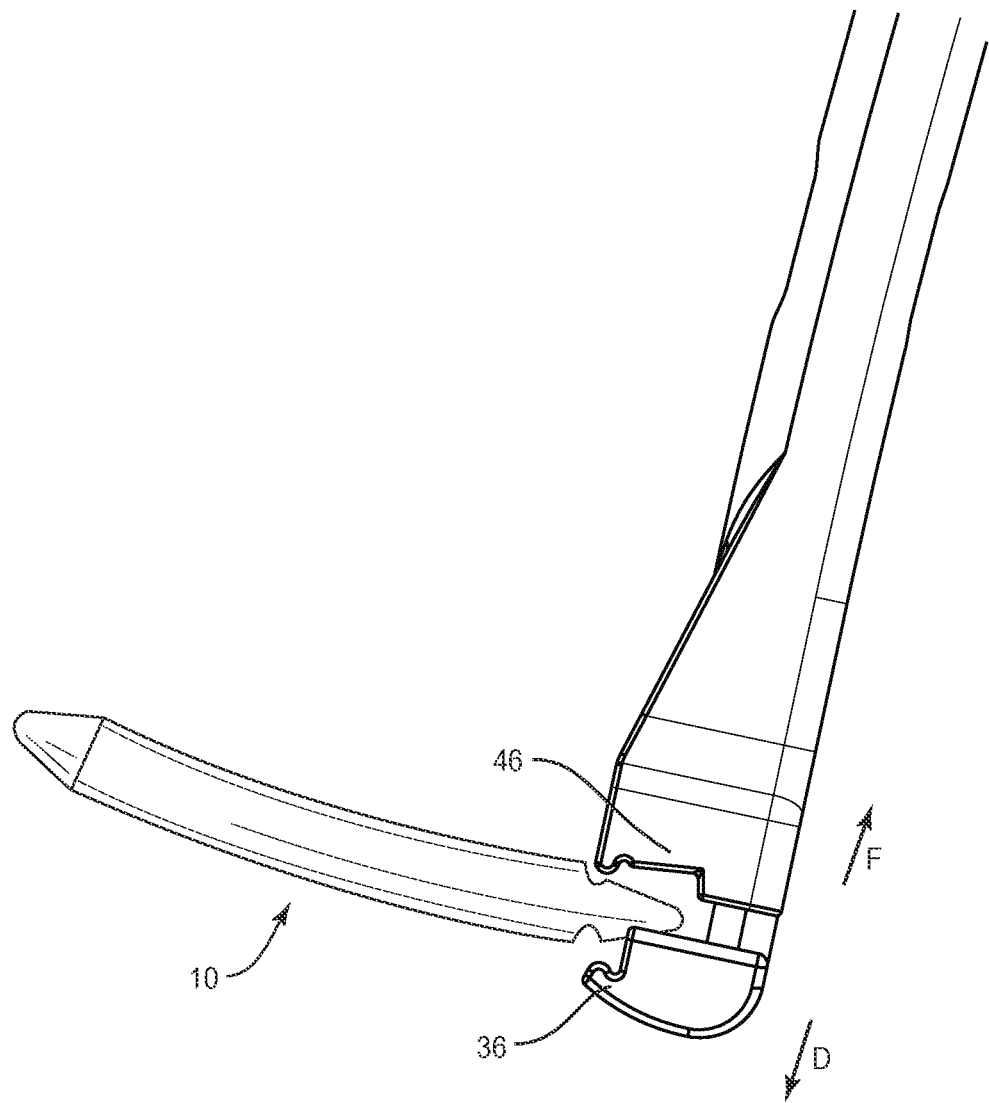
FIG. 7 is an enlarged break away view of the components shown in FIG. 6.
Figure 8:
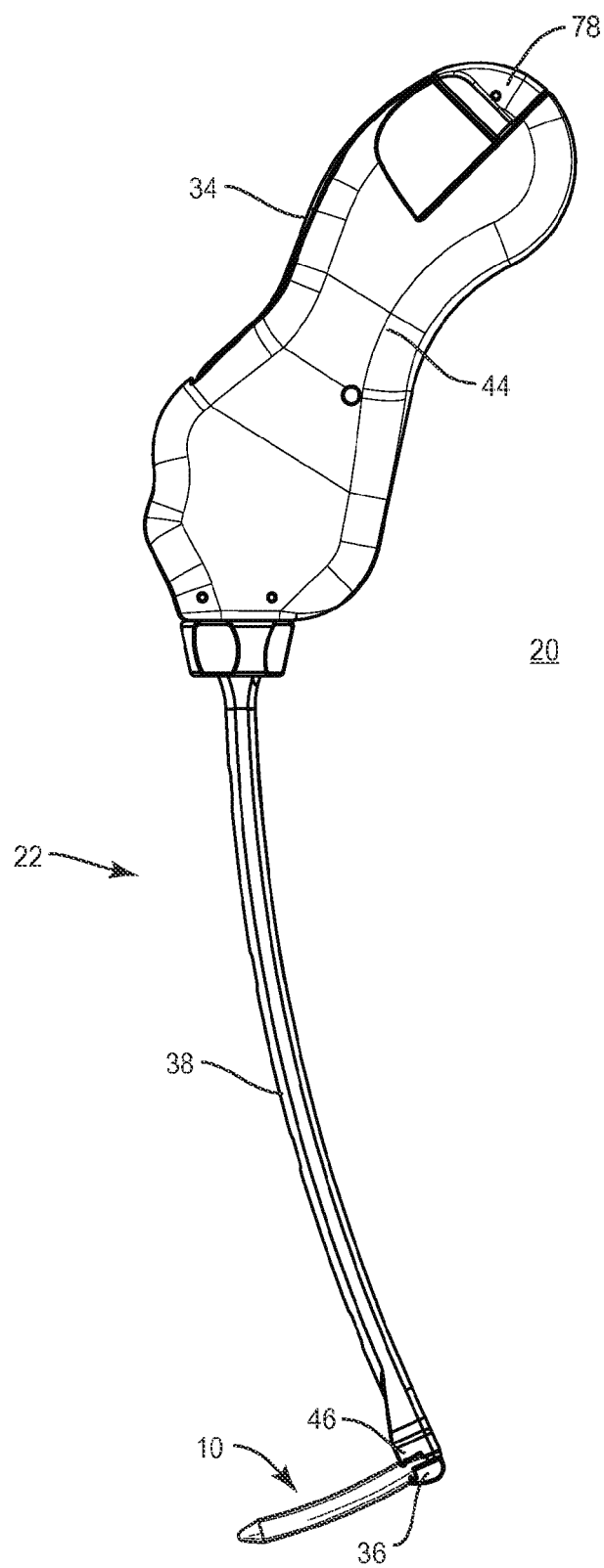
FIG. 8 is a side view of the components shown in FIG. 6.

In operation, instrument 22 is selectively movable between a non-locking orientation, as shown in FIGS. 6 and 7, and a locking orientation, as shown in FIG. 8. In the locking orientation, jaws 36, 46 are disposed in a capturing engagement with spinal rod 10. To release spinal rod 10 from jaws 36, 46, a force, in the direction shown by arrow A in FIG. 4, is applied to release handle 78 to actuate collet release 68. Surface 87 is released from ledge 90 such that latch 34 is rotatable relative to handle body 44 about pivot point 70. Latch 34 rotates, in the direction shown by arrow B in FIG. 5, via spring 64, to dispose latch 34 in a non-locking orientation. Latch 34 rotates and bead 30 is disposed with end 74 of slot 32 and latch 34 protrudes from handle body 44.

Rotation of latch 34 to the non-locking orientation causes shaft 24 to axially translate, in the direction shown by arrow D in FIGS. 6 and 7, relative to handle body 44 and sleeve 38. Bead 30 translates along slot 32 to end 72 to facilitate axial translation of shaft 24 during rotation of latch 34. The axial translation of shaft 24 causes jaw 36 to separate from jaw 46 to release spinal rod 10 from capture.

From the non-locking orientation, latch 34 can be rotated such that instrument 22 is disposable in the locking orientation, for example, such that jaws 36, 46 engage and capture spinal rod 10. From the non-locking orientation, a force is applied to latch 34, in the direction shown by arrow E in FIG. 6, causing latch 34 to rotate in the direction shown by arrow E to close jaws 36, 46 such that shaft 24 axially translates, in the direction shown by arrow F in FIGS. 6 and 7, relative to handle body 44 and sleeve 38 to capture spinal rod 10 and dispose instrument 22 in the locking orientation, as shown in FIG. 8. Rotation of latch 34 to its locking orientation facilitates translation of collet release 68 such that spring 76 biases collet release 68 to the locking orientation, as described, such that collet release 68 automatically returns to the locking orientation.

Figure 9:
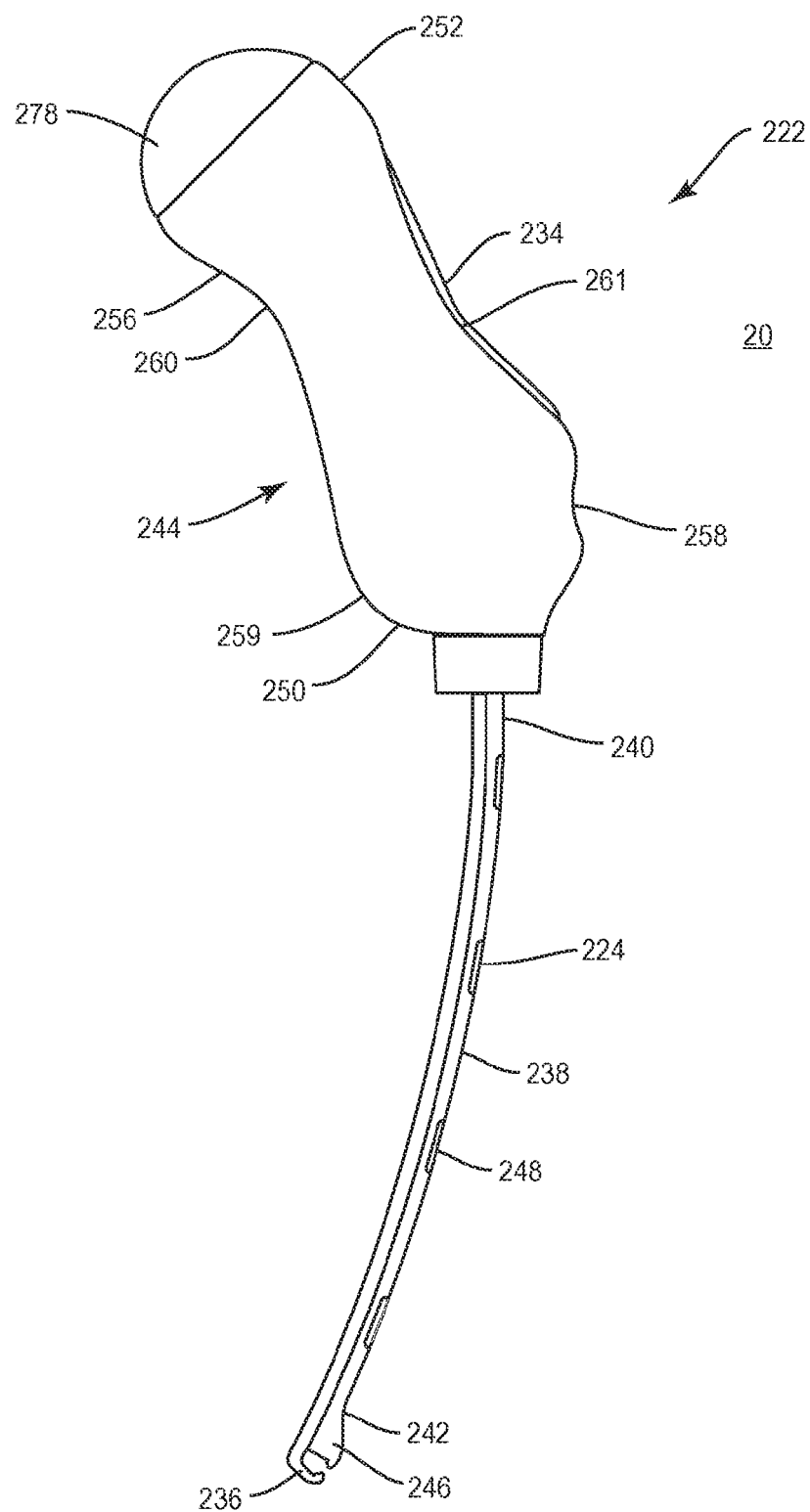
FIG. 9 is a side view of components of one embodiment of a surgical implant system in accordance with the principles of the present disclosure.
Figure 10:
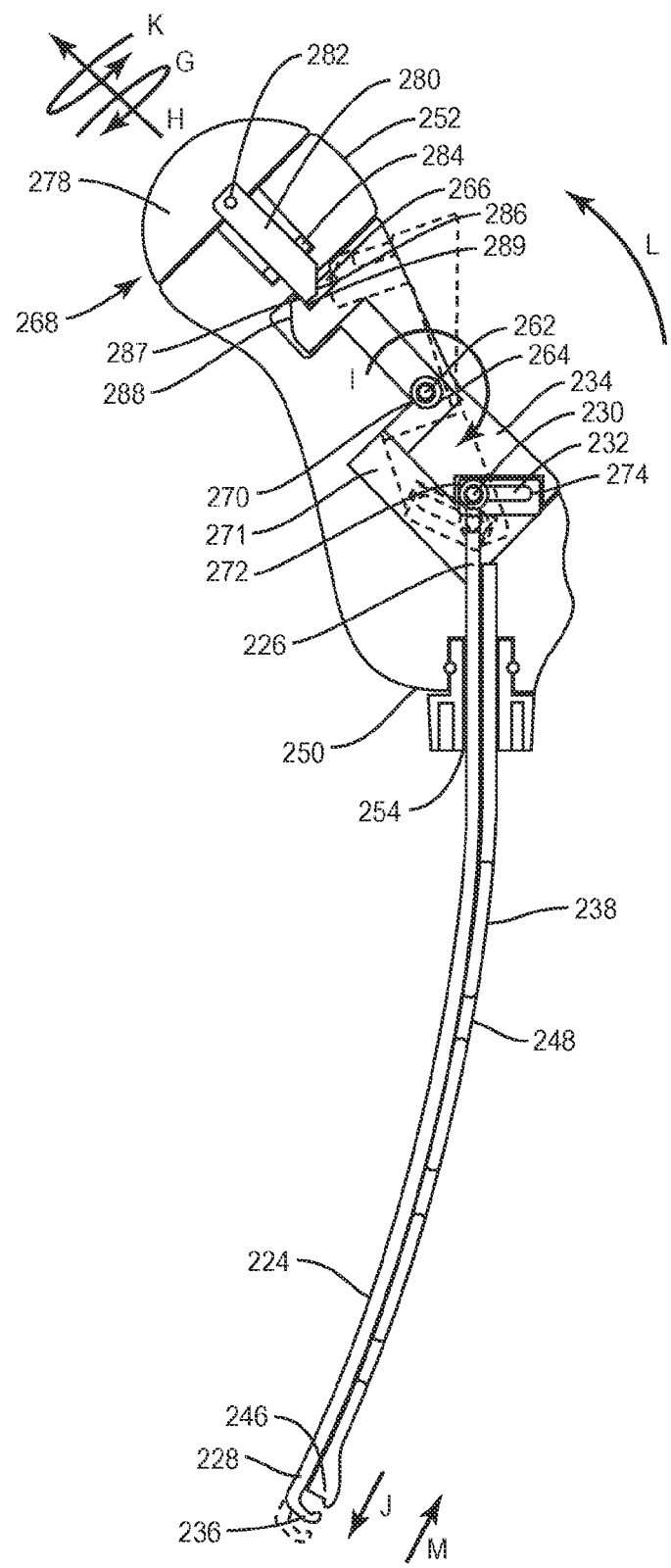
FIG. 10 is a side view of the components shown in FIG. 9.

In one embodiment, as shown in FIGS. 9 and 10, system 20, similar to the systems described above with regard to FIGS. 1-8, comprises an instrument 222, similar to instrument 12, described above, configured for engagement with spinal rod 10.

Instrument 222 includes a first member, such as, for example, a flexible inner shaft 224 extending between an end 226 and an end 228, similar to shaft 24 described above. End 226 includes a bead 230 configured for translation within a slot 232 of a latch 234, similar to latch 34 described above. End 228 includes a clamp, such as, for example, a jaw 236, similar to jaw 36 described above.

Instrument 222 includes a second member, such as, for example, an outer sleeve 238, similar to sleeve 38 described above. Sleeve 238 extends between an end 240 and an end 242. End 240 is configured for fixed engagement with an interior surface (not shown) of a handle body 244, similar to handle body 44 described above. End 242 includes a clamp, such as, for example, a jaw 246, similar to jaw 46 described above. Jaws 236, 246 comprise a collet of instrument 222. Relative movement of jaws 236, 246 is facilitated with relative axial translation of shaft 224 and sleeve 238.

Sleeve 238 defines a T-shaped cavity configured for disposal of correspondingly shaped beads of shaft 224, similar to that described with regard to sleeve 38 and shaft 24 above. Sleeve 238 has an arcuate curvature, which defines a radius of curvature, extending between ends 240, 242. Sleeve 238 includes a plurality of openings 248 to provide visualization of shaft 224, disposal of the beads and cleaning.

Handle body 244 extends between an end 250 and an end 252. End 250 is configured for fixed engagement with end 240 of sleeve 238. Handle body 244 has an arcuate curvature, which defines a radius of curvature, extending between ends 250, 252. End 250 defines a cavity 254 configured for disposal of a portion of shaft 224. In one embodiment, the radius of handle body 244 is substantially equivalent to the radius of sleeve 238. In one embodiment, the radius of handle body 244 is substantially offset from the radius of sleeve 238.

Handle body 244 includes an outer surface 256 that defines finger grooves 258 and a thumb groove 260. In one embodiment, outer surface 256 defines finger grooves 259 disposed opposite finger grooves 258 and a thumb groove 261 disposed opposite thumb groove 260.

Handle body 244 defines a cavity 271 configured for disposal of a third member, such as, for example, an actuator, which includes a part, such as, for example, latch 234 mounted with handle body 244. Latch 234 is resiliently biased for rotation relative to handle body 244 by a biasing member, such as, for example, a torsion spring 264.

Spring 264 is centrally disposed within handle body 244 between ends 250, 252 and rotates latch 234 between a locking orientation, as shown in FIG. 9, and a non-locking orientation, as shown in phantom in FIG. 10, to release spinal rod 10 from jaws 236, 246. In some embodiments, from the non-locking orientation, latch 234 can be manually drawn open such that jaws 236, 246 are caused to open wider and/or for disassembly of the components of instrument 222.

Latch 234 defines a cavity 266 configured for disposal of at least a portion of a locking element, such as, for example, a collet release 268, similar to collet release 68 described above. Latch 234 includes a pin 262 disposed through a thickness of latch 234 at a central location of latch 234. Latch 234 is connected to handle body 244 via pin 262 at a pivot point 270 centrally disposed between ends 250, 252 of handle body 244 for rotation of latch 234 relative to handle body 244.

Latch 234 and shaft 224 are connected such that rotation of latch 234 about pivot point 270 causes axial translation of shaft 224 within and relative to sleeve 238. For example, latch 234 can include slot 232 configured for translation of bead 230 of shaft 224 between movable limits provided by the surface that defines slot 232. Slot 232 extends between a first movable limit, such as, for example, an end 272 and a second movable limit, such as, for example, an end 274 having a uniform thickness therebetween. Bead 230 is translatable between ends 272 and 274.

Collet release 268 is resiliently biased to engage latch 234 via a biasing member, such as, for example, a coil spring (not shown) disposed within handle body 244. Collet release 268 includes a first portion, such as, for example, a release handle 278 and a second portion, such as, for example, a lock 280 extending therefrom. Release handle 278 has a semi-circular shape and is dimensioned such that release handle 278 and end 252 of handle body 244 are disposed in a flush engagement in a locking orientation of collet release 268. Release handle 278 is connected to lock 280 via a pin 282.

Release handle 278 is manipulable to a non-locking orientation to release latch 234 for rotation to the non-locking orientation of latch 234 such that the coil spring is compressed between a flange 284 of lock 280 and release handle 278. In the non-locking orientation of collet release 268, the coil spring is configured to bias lock 280 into a locking orientation with latch 234. Lock 280 includes an inclined ramp 286 configured for engagement with an inclined ramp 288 of latch 234. Ramp 288 engages ramp 286 as latch 234 is rotated to the locking orientation of latch 234, as shown in FIG. 10, to facilitate engagement of lock 280 with latch 234 and disposal of release handle 278 in the locking orientation of collet release 268. Lock 280 includes a surface 287 disposed adjacent inclined ramp 286 configured for engagement with an inner wall 289 of cavity 266 to retain latch 234 in a locking orientation.

Figure 20:
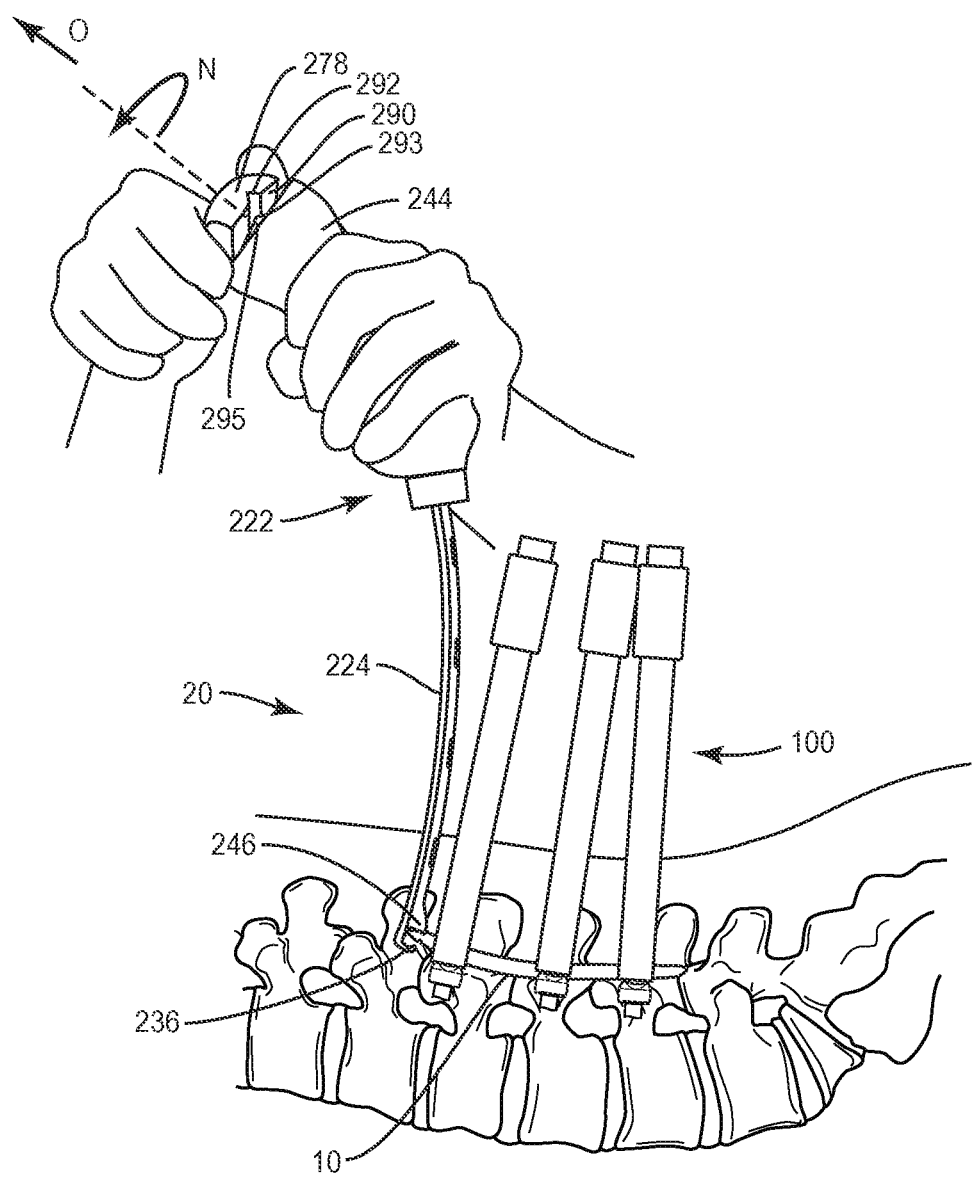
FIG. 20 is a side view of the components shown in FIG. 11 disposed with the body.

A cam surface 290, as shown in FIG. 20, of release handle 278 defines a groove 292 having a V-shaped cross section. Groove 292 is configured for engagement and mating with a cam surface 293 of handle body 244 that defines a wedge 295 having a V-shaped cross section. For example, in the locking orientation of collet release 268, as shown in FIG. 10, wedge 295 is disposed in groove 292 and release handle 278 is disposed in flush engagement with handle body 244. As release handle 278 is rotated, the surface of groove 292 slides along wedge 295 separating release handle 278 from handle body 244 in an axial direction. Lock 280 is drawn in an axial direction such that surface 287 is released from inner wall 289. Latch 234 is rotatable from the locking orientation to the non-locking orientation, as shown in phantom in FIG. 10. In one embodiment, release handle 278 is rotated, in a plane transverse to the longitudinal axis of handle body 244, between the locking orientation and the non-locking orientation to release lock 280 from latch 234 and/or to engage lock 280 with latch 234. In one embodiment, release handle 278 is drawn axially between the locking orientation and the non-locking orientation to release lock 280 from latch 234 and/or to engage lock 280 with latch 234.

In operation, instrument 222 is selectively movable between a non-locking orientation, as shown in phantom in FIG. 10 and similar to that shown and described in FIG. 6, and a locking orientation, as shown in FIG. 10 and similar to that shown and described in FIG. 8. In the locking orientation, jaws 236, 246 are disposed in a capturing engagement with spinal rod 10. Bead 230 is disposed with end 272 of slot 232 and latch 234 is disposed in flush alignment with handle body 244.

To release spinal rod 10 from jaws 236, 246, release handle 278 is rotated, for example, in the direction shown by arrow G in FIG. 10, to actuate collet release 268. As release handle 278 is rotated, the surface of groove 292 slides along wedge 295 separating release handle 278 from handle body 244, in the axial direction shown by arrow H. Lock 280 is drawn in the axial direction such that surface 287 is released from inner wall 289 such that latch 234 is rotatable relative to handle body 244 about pivot point 270. Latch 234 rotates, in the direction shown by arrow I, for disposal in the non-locking orientation. Latch 234 rotates and protrudes from handle body 244.

Rotation of latch 234 to the non-locking orientation causes shaft 224 to axially translate, in the direction shown by arrow J, relative to handle body 244 and sleeve 238. Bead 230 translates along slot 232 for disposal with end 274 to facilitate axial translation of shaft 224 during rotation of latch 234, as shown in phantom. The axial translation of shaft 224 causes jaw 236 to separate from jaw 246 to release spinal rod 10 from capture.

From the non-locking orientation, latch 234 can be rotated such that instrument 222 is disposable in the locking orientation, for example, such that jaws 236, 246 engage and capture spinal rod 10. From the non-locking orientation, release handle 278 is rotated, for example, in the direction shown by arrow K, such that the surface of groove 292 slides along wedge 295. In some embodiments, release handle 278 can be rotated in either direction to lock and unlock latch 234. In some embodiments, release handle 278 is rotated in a first direction to lock latch 234 and then rotated in an opposite direction to unlock latch 234. Wedge 295 is aligned with groove 292 for disposal therein and release handle 278 is disposed in flush engagement with handle body 244. Lock 280 is biased to the locking orientation of collet release 268.

Latch 234 is rotated, in the direction shown by arrow L, such that ramp 288 engages and slides over ramp 286, as facilitated by the resilient bias of lock 280, to dispose latch 234 in the locking orientation. Surface 287 and inner wall 289 engage to prevent rotation of latch 234 from the locking orientation. Rotation of latch 234 to the locking orientation causes shaft 224 to axially translate, in the direction shown by arrow M, relative to handle body 244 and sleeve 238, to close jaws 236, 246 and capture spinal rod 10.

System 20 includes a plurality of extenders 100, as shown in FIGS. 11-20, configured for connection with bone fasteners and to facilitate disposal of spinal rod 10 with bone fasteners. Each extender 100 extends between a proximal end 102 and a distal end 104. Each extender 100 includes a first wall, such as, for example, a rail 106 and a second wall, such as, for example, a rail 108. Rails 106, 108 define a passageway 110 therebetween. Passageway 110 includes an implant cavity 112, which defines a width dimension w1 between rails 106, 108 configured for the passage of at least a portion of spinal rod 10. Passageway 110 has a uniform thickness. In some embodiments, all or only a portion of passageway 110 may have alternate cross section configurations, such as, for example, oval, oblong, triangular, square, polygonal, irregular, uniform, non-uniform, offset, staggered, and/or tapered.

In assembly, operation and use, system 20, similar to the systems described above, is employed with a surgical procedure for treatment of a spinal disorder affecting a section of a spine of a patient, as shown in FIGS. 11-20. For example, system 20 can be used with a surgical procedure for treatment of a condition or injury of an affected section of the spine including vertebrae V. System 20 may be employed with other surgical procedures, such as, for example, the systems and methods shown and described in U.S. Patent Application Publication No. 2008/0269805 to Dekutowski et al., the entire contents of which being hereby incorporated by reference herein. In some embodiments, system 20 may be employed with other surgical procedures, such as, for example, those described herein.

In use, to treat the affected section of vertebrae V, a medical practitioner obtains access to a surgical site including vertebrae V in any appropriate manner, such as through incision and retraction of tissues. In some embodiments, system 20 may be used in any existing surgical method or technique including open surgery, mini-open surgery, minimally invasive surgery including percutaneous surgical implantation, whereby vertebrae are accessed through a micro-incision, or sleeve that provides a protected passageway to the area. Once access to the surgical site is obtained, the particular surgical procedure is performed for treating the spinal disorder. The components of system 20 are employed to augment the surgical treatment. The components of system 20 can be delivered or implanted as a pre-assembled device or can be assembled in situ. One or all of the components of system 20 may be completely or partially revised, removed or replaced during or after the surgical procedure.

One or a plurality of incisions are made in the body of a patient and a cutting instrument (not shown) creates one or a plurality of surgical pathways and/or openings for implantation of components of system 20. For example, system 20 is employed with a percutaneous surgical implantation such that a stab incision creates a surgical pathway for delivering a bone fastener, such as, for example, a pedicle screw 101 and/or spinal rod 10 to the surgical site. A preparation instrument (not shown) can be employed to prepare tissue surfaces of vertebrae V, as well as for aspiration and irrigation of a surgical region according to the requirements of a particular surgical application.

Pilot holes or the like are made in vertebrae V for receiving the shafts of pedicle screws 101. Components of system 20 including extenders 100 are disposed adjacent vertebrae V at the surgical site and the components of system 20 are manipulable to fix or otherwise connect pedicle screws 101 with vertebrae V, according to the particular requirements of the surgical treatment. Pedicle screws 101 are fastened with vertebrae V. A driver (not shown) may be employed with extenders 100 to fix pedicle screws 101 with vertebrae V.

Jaws 236, 246 are disposed adjacent spinal rod 10 and in a non-locking and open orientation, as described with regard to FIGS. 9 and 10. From the non-locking orientation, release handle 278 is rotated for disposal in flush engagement with handle body 244, as described. Latch 234 is rotated to the locking orientation such that shaft 224 axially translates relative to handle body 244 and sleeve 238 to close jaws 236, 246 and capture spinal rod 10. In one embodiment, spinal rod 10 is initially placed, inclined relative to extenders 100, in the stab incision percutaneously and moved to the surgical site such that spinal rod 10 is inclined relative to extenders 100.

Figure 11:
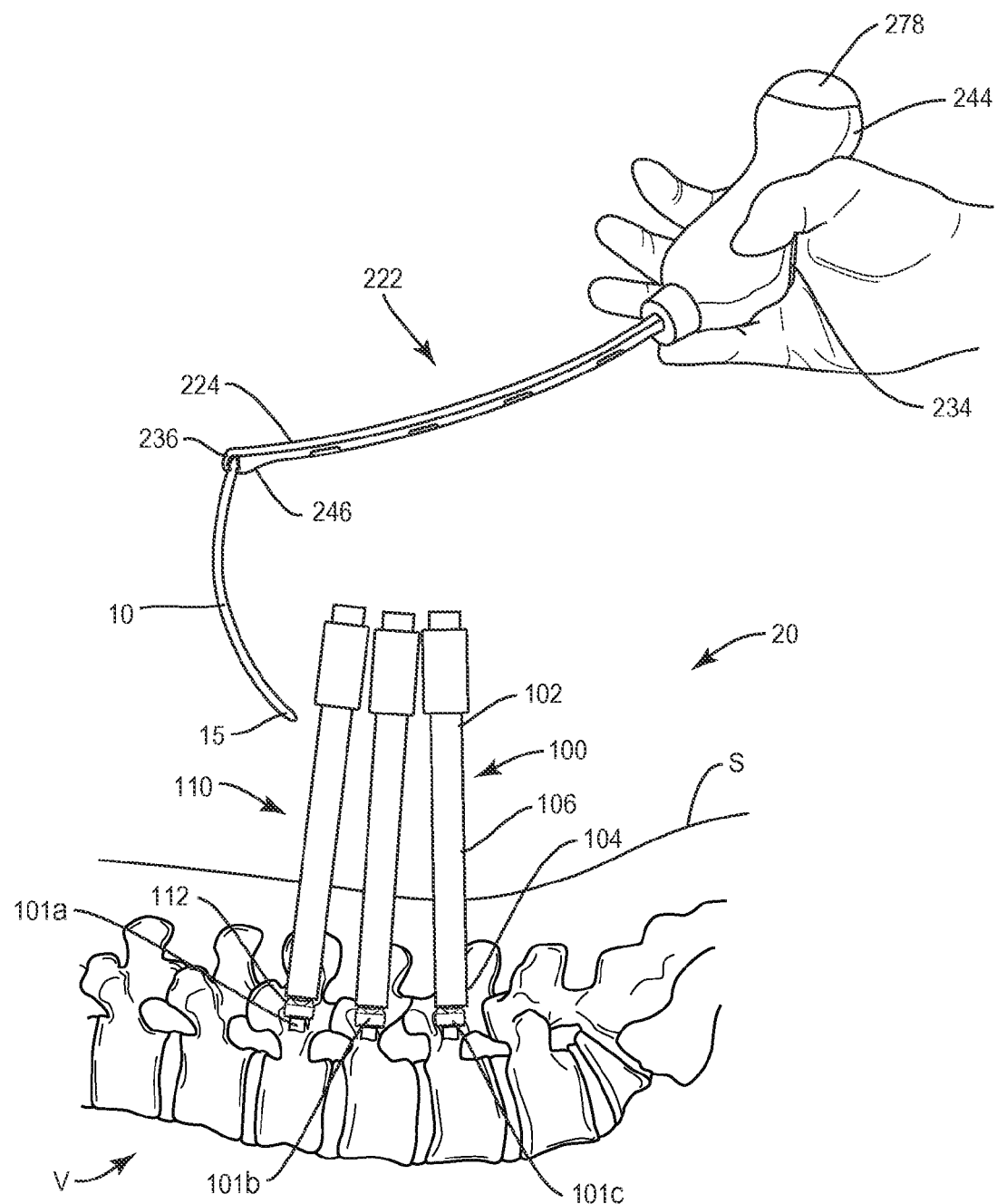
FIG. 11 is a side view of components of one embodiment of a surgical implant system in accordance with the principles of the present disclosure disposed with a body.

In one embodiment, as shown in FIGS. 11-16, a practitioner employs instrument 222 for insertion of spinal rod 10 through extenders 100 along a path that includes a distal and/or far location from the practitioner of the path corresponding to an adjacent pedicle screw 101a, to a proximal and/or near location to the practitioner of the path corresponding to an adjacent pedicle screw 101c. Spinal rod 10 is disposed with instrument 222 in the locking orientation, as shown in FIG. 11.

Figure 12:
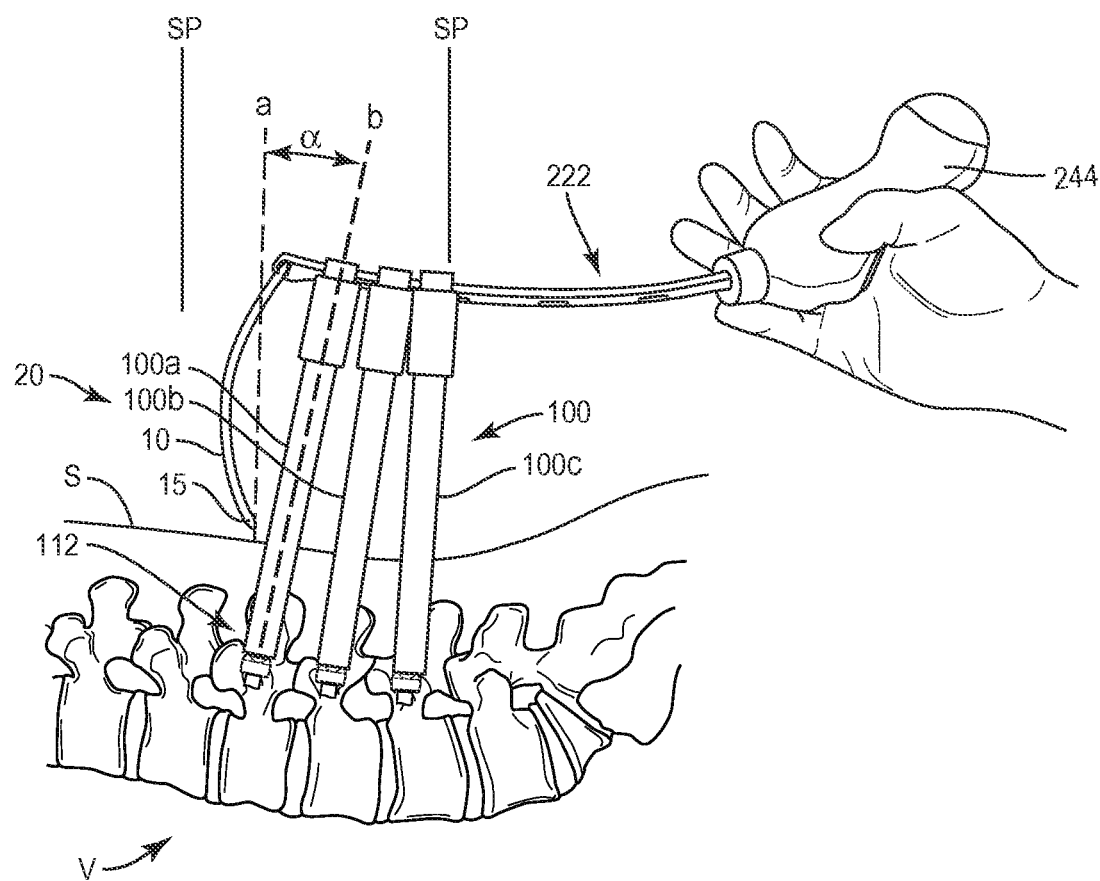
FIG. 12 is a side view of the components shown in FIG. 11 disposed with the body.
Figure 13:
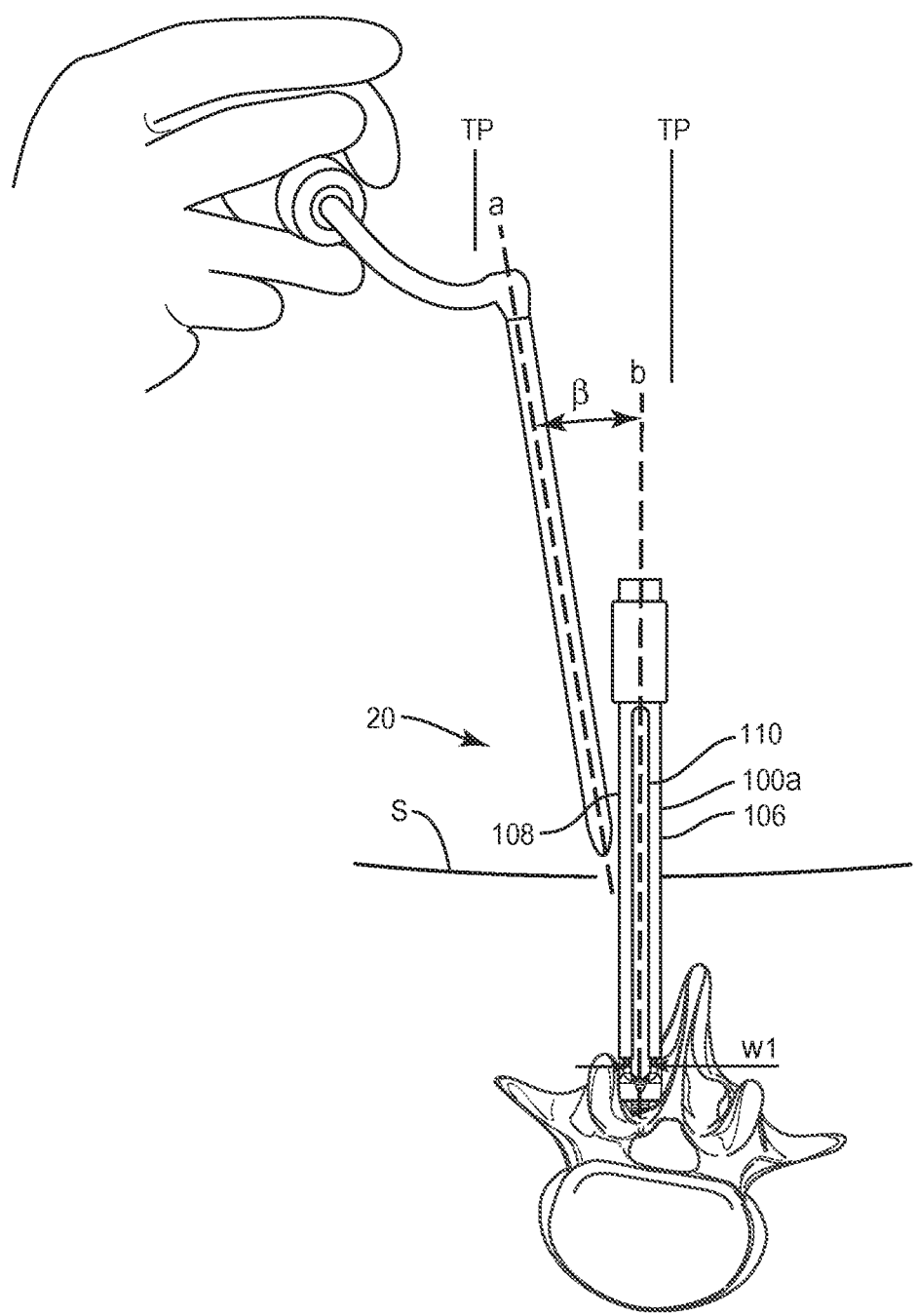
FIG. 13 is an end view of the components shown in FIG. 11 disposed with the body.

The practitioner grips handle 244 to dispose a distal tip 15 of spinal rod 10 inside the window of extender 100a and above the skin and fascia S, as shown in FIG. 12. Instrument 222 orients spinal rod 10 such that an axis a of spinal rod 10 is offset an angle α from an axis b of extender 100a. Angle α is disposed in a first plane, such as, for example, a sagittal plane SP of vertebrae V. In some embodiments, angle α is oriented in a cephalad-caudal orientation. In some embodiments, angle α may be oriented in planes, such as those described herein.

In some embodiments, instrument 222 orients spinal rod 10 such that axis a is offset an angle β from axis b. Angle β is disposed in a second plane, such as, for example, a transverse plane TP of vertebrae V. In some embodiments, angle β is oriented in a medial orientation and/or a lateral orientation. In some embodiments, angle β may be oriented in planes, such as those described herein. In some embodiments, instrument 222 is oriented at angle α and/or angle β to prevent handle body 244 from interfering with extenders 100. In some embodiments, instrument 222 orients spinal rod 14 at angle α and angle β, disposed relative extender 100a, to define a three dimensional angle, which is defined by a position in space of spinal rod 10 and the intersection of planes SP, TP.

Figure 14:
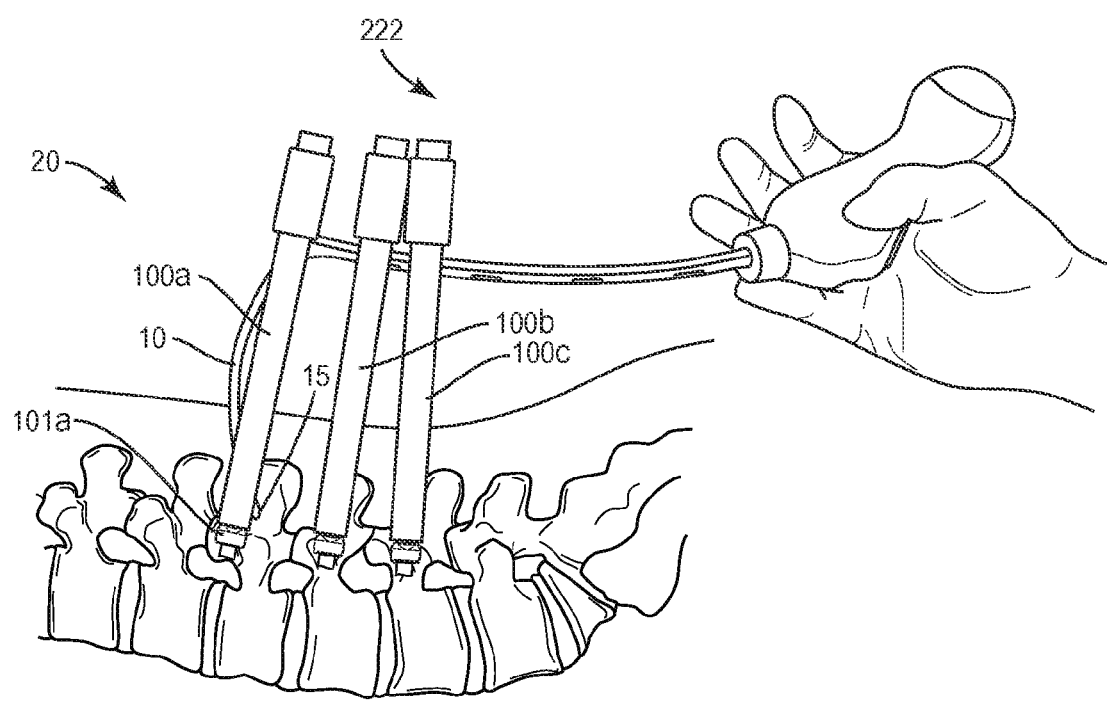
FIG. 14 is a side view of the components shown in FIG. 11 disposed with the body.
Figure 15:
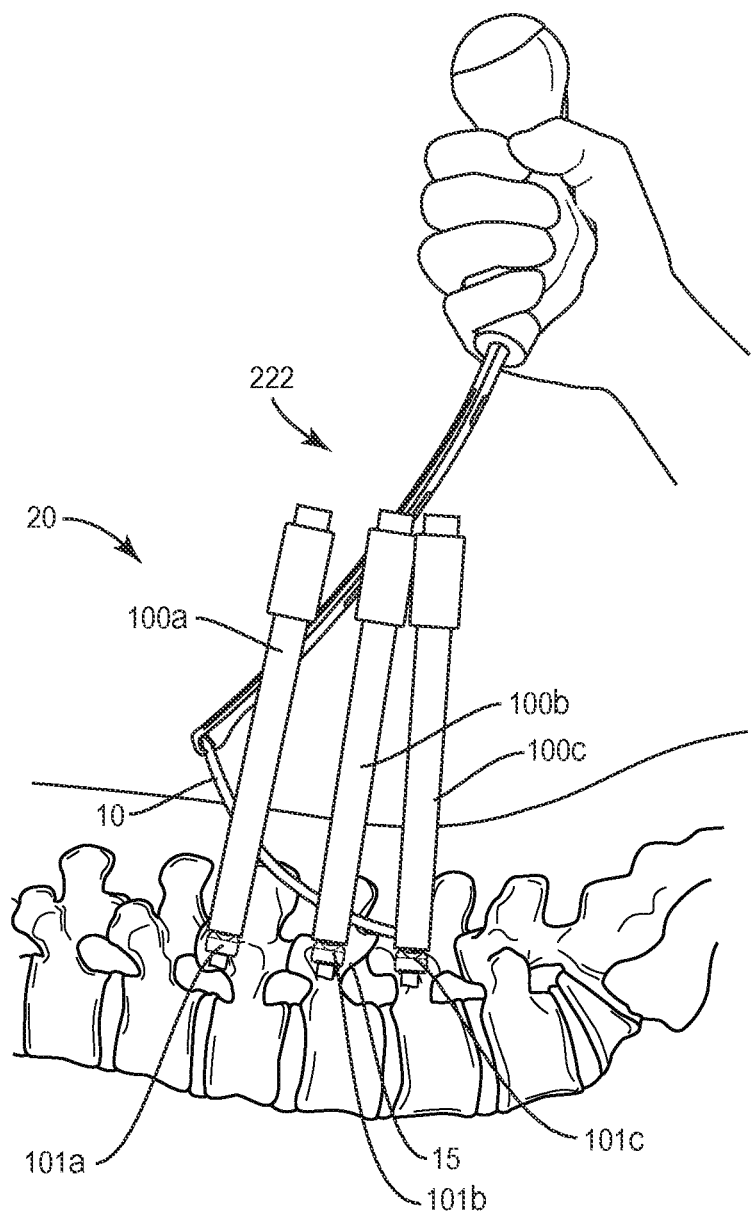
FIG. 15 is a side view of the components shown in FIG. 11 disposed with the body.
Figure 16:
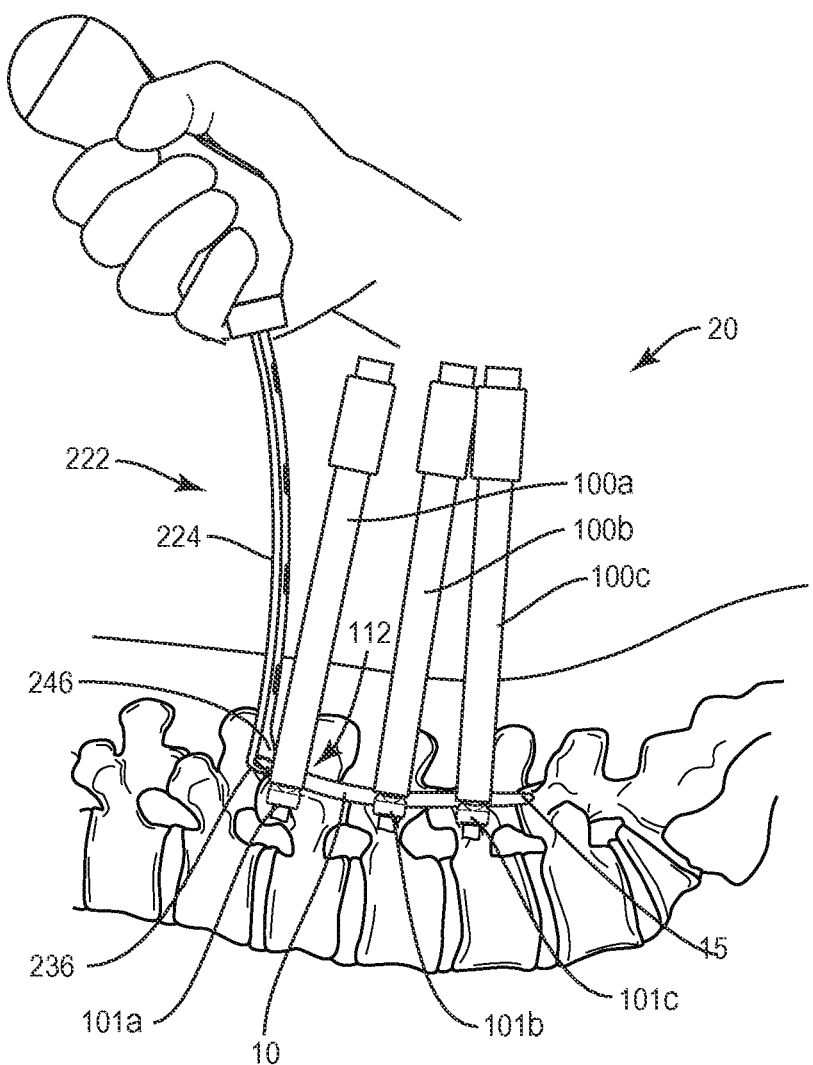
FIG. 16 is a side view of the components shown in FIG. 11 disposed with the body.

With distal tip 15 disposed beneath the skin and fascia and adjacent extender 100a, as shown in FIG. 14, instrument 222 orients spinal rod 10 to simultaneously lower spinal rod 10 to the screw head of pedicle screw 101a and rotate spinal rod 10 through extenders 100b, 100c, as shown in FIG. 15. Instrument 222 orients spinal rod 10 to lower spinal rod 10 with the screw heads of pedicle screws 101b, 101c, as shown in FIG. 16. Jaws 236, 246 have a greater width dimension than the window of extender 100a and are prevented from entering the window of extender 100a and/or implant cavity 112. In some embodiments, one or more of extenders 100 are configured for engagement with a reduction instrument, which is disposed for translation along passageway 110 to engage spinal rod 10 and reduce spinal rod 10 into the screw heads of the pedicle screws.

In one embodiment, as shown in FIGS. 17-20, similar to the method described with regard to FIGS. 11-16, a practitioner employs instrument 222 for insertion of spinal rod 10 through extenders 100 along a path that includes a proximal and/or near location to the practitioner of the path corresponding to an adjacent pedicle screw 101a, to a distal and/or far location from the practitioner of the path corresponding to an adjacent pedicle screw 101c. Spinal rod 10 is disposed with instrument 222 in the locking orientation, as described.

Figure 17:
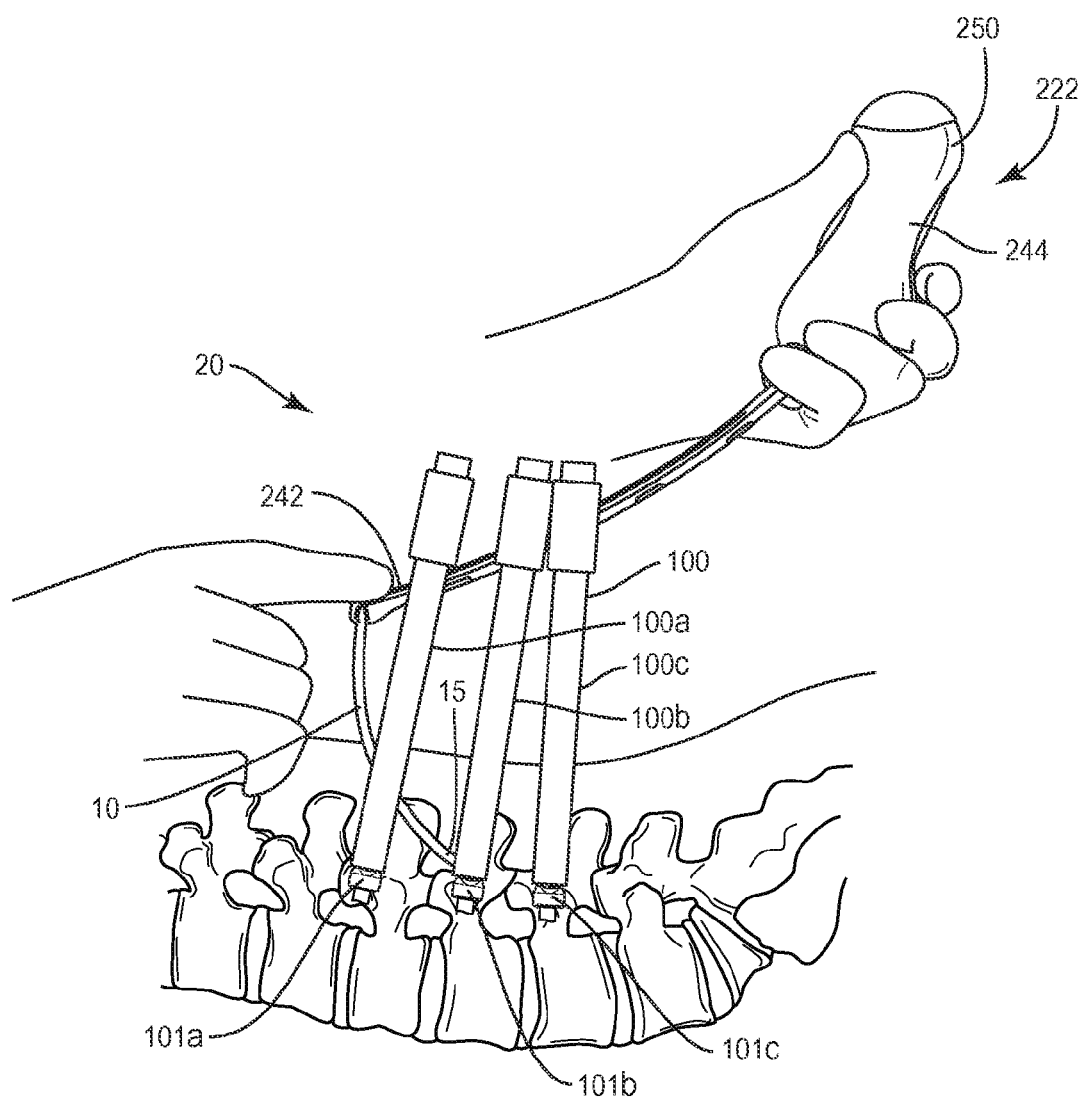
FIG. 17 is a side view of the components shown in FIG. 11 disposed with the body.

The practitioner grips handle 244 to dispose distal tip 15 inside the window of extender 100a and within implant cavity 112, as shown in FIG. 17. Instrument 222 orients spinal rod 10, similar to that described with regard to FIGS. 12 and 13.

Figure 18:
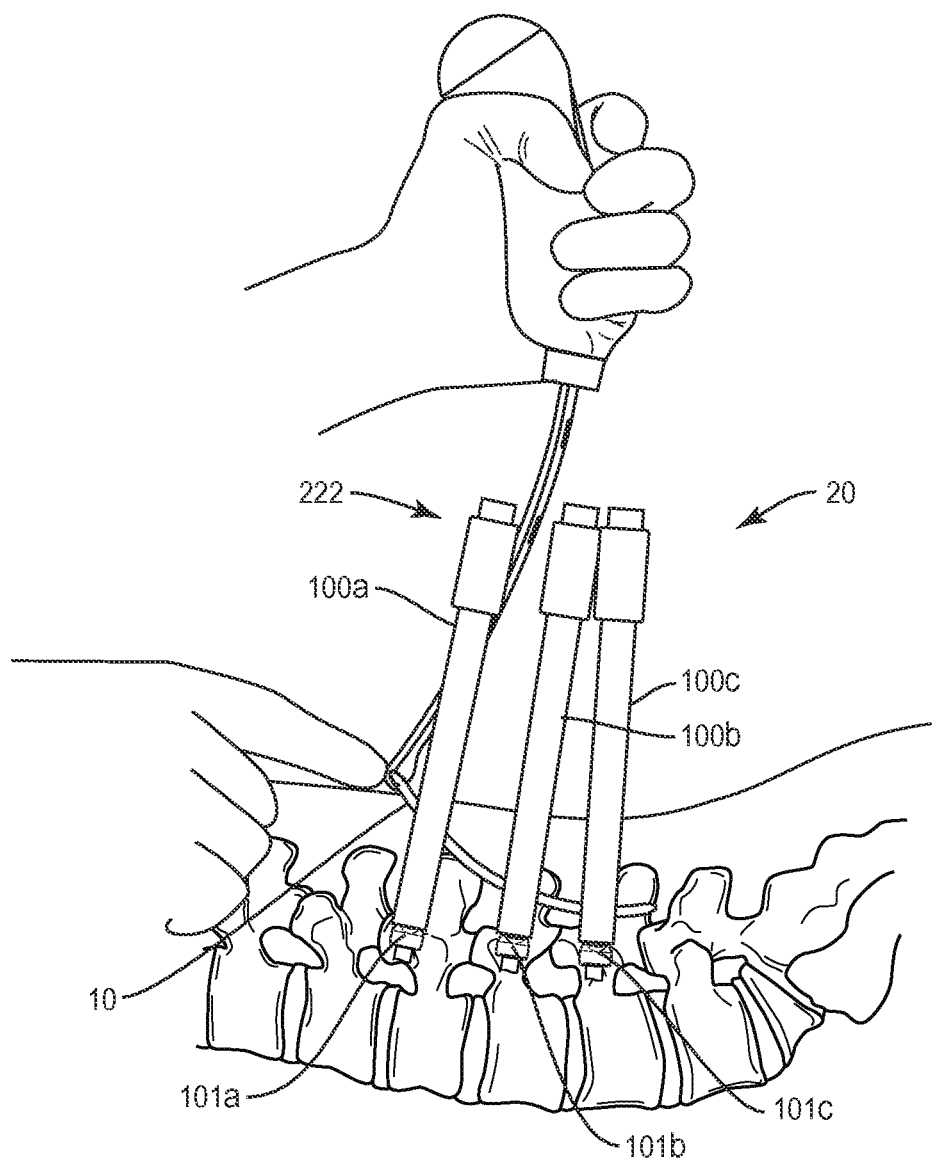
FIG. 18 is a side view of the components shown in FIG. 11 disposed with the body.

With distal tip 15 disposed beneath the skin and fascia and adjacent extender 100a, as shown in FIG. 17, instrument 222 orients spinal rod 10 to simultaneously lower spinal rod 10 to the screw head of pedicle screw 101a and rotate spinal rod 10 through extenders 100b, 100c, as shown in FIG. 18. Instrument 222 orients spinal rod 10 to lower spinal rod 10 with the screw heads of pedicle screws 101b, 101c. In some embodiments, the incision through which spinal rod 10 is inserted may need to be extended up to approximately 10 millimeters to accommodate the length of jaws 236, 246.

Figure 19:
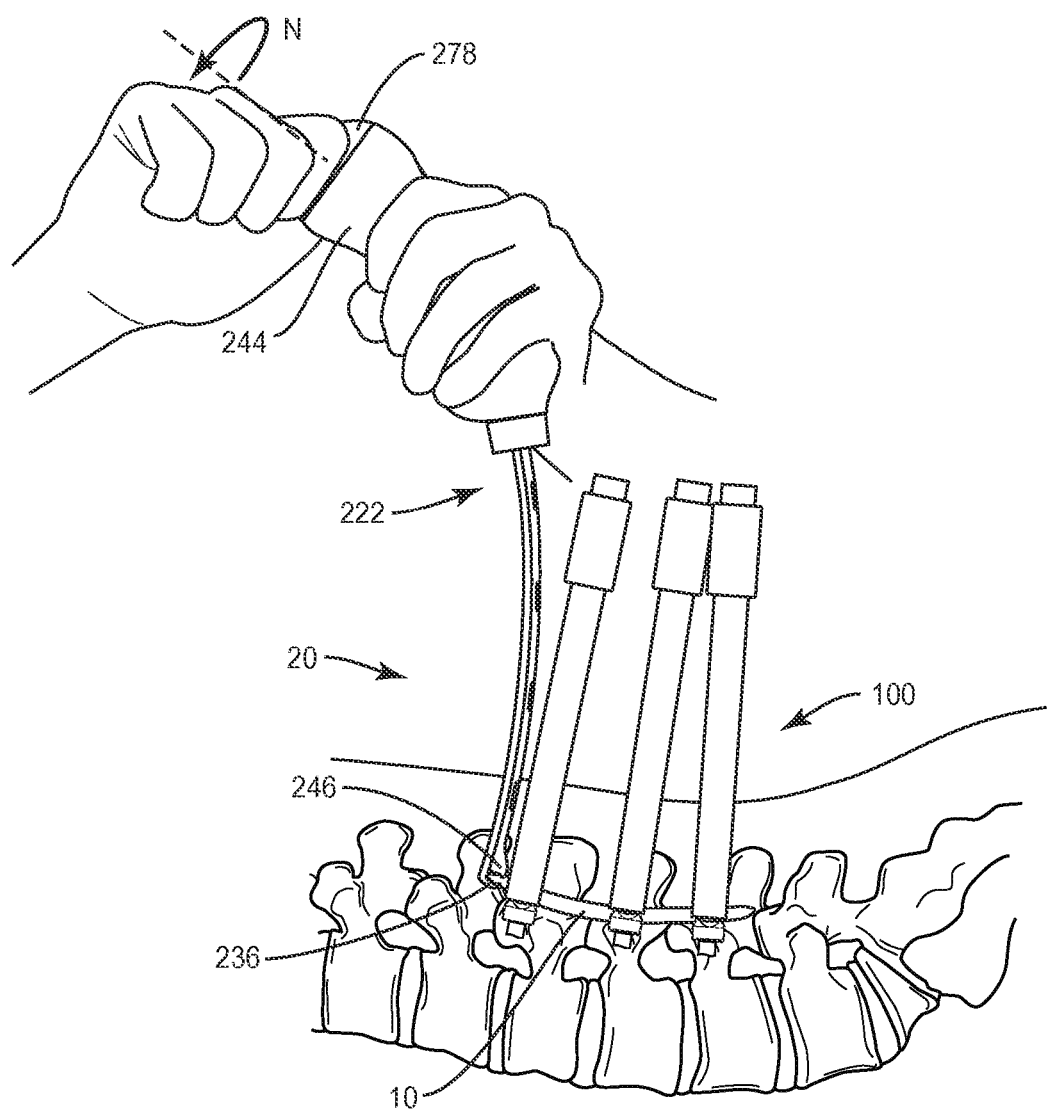
FIG. 19 is a side view of the components shown in FIG. 11 disposed with the body.

To release spinal rod 10 from jaws 236, 246, release handle 278 is rotated, in the direction shown by arrow N in FIG. 19, to actuate collet release 268. As release handle 278 is rotated, the surface of groove 292 slides along wedge 295 separating release handle 278 from handle body 244, in the axial direction shown by arrow O in FIG. 20. Lock 280 is drawn in the axial direction such that surface 287 is released from inner wall 289 such that latch 234 is rotatable relative to handle body 244 about pivot point 270, as described herein.

Rotation of latch 234 to the non-locking orientation causes shaft 224 to axially translate relative to handle body 244 and sleeve 238, as described herein. The axial translation of shaft 224 causes jaw 236 to separate from jaw 246 to release spinal rod 10 from capture. Spinal rod 10 is locked with pedicle screws 101 by coupling members, such as, for example, set screws. Instrument 222 and/or the non-implanted components of system 20 are removed from the surgical site and the incision is closed.

One or more of the components of system 20 can be made of radiolucent materials such as polymers. Radiomarkers may be included for identification under x-ray, fluoroscopy, CT or other imaging techniques. In some embodiments, the use of microsurgical and image guided technologies may be employed to access, view and repair spinal deterioration or damage, with the aid of system 20.

In some embodiments, system 20 may include one or a plurality of spinal rods and/or bone fasteners for use with a single vertebral level or a plurality of vertebral levels. In some embodiments, the rods and/or bone fasteners may be engaged with vertebrae in various orientations, such as, for example, series, parallel, offset, staggered and/or alternate vertebral levels. In some embodiments, the bone fasteners may include one or a plurality of multi-axial screws, sagittal angulation screws, pedicle screws, mono-axial screws, uniplanar screws, fixed screws, tissue penetrating screws, conventional screws, expanding screws, anchors, buttons, connectors, clips, snaps, friction fittings, compressive fittings, expanding rivets, staples, nails, adhesives, fixation plates and/or posts. The spinal rods and/or bone fasteners may be coated with an osteoinductive or osteoconductive material to enhance fixation, and/or include one or a plurality of therapeutic agents.

In one embodiment, system 20 includes an agent, which may be disposed, packed, coated or layered within, on or about the components and/or surfaces of system 20. In some embodiments, the agent may include bone growth promoting material, such as, for example, bone graft to enhance fixation of the fixation elements with vertebrae. In some embodiments, the agent may include one or a plurality of therapeutic agents and/or pharmacological agents for release, including sustained release, to treat, for example, pain, inflammation and degeneration.

In some embodiments, system 20 may include one or a plurality of inserters, extenders, reducers, bone fasteners, rods and/or other vertebral constructs, which may be alternately sized and dimensioned, and arranged as a kit, according to the requirements of a particular application.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a body;
   a first member extending between a proximal end and a distal end;
   a second member extending between a proximal end connected with the body and a distal end; and
   a third member connected to the proximal end of the first member and the body to relatively axially translate the distal ends, the third member including a latch and a lock engageable with the latch,
   wherein the latch is disposable in a locking orientation such that the distal ends engage a spinal construct and rotatable to a non-locking orientation such that the lock disengages the latch and the latch is biased relative to the body such that the distal ends are disposed to disengage the spinal construct, the distal end of the first member being distal to the distal end of the second member when the latch is in the non-locking orientation and the locking orientation.

2. A surgical instrument as recited in claim 1, wherein the third member includes an outer surface having a plurality of widths, the widths having an ergonomic configuration to facilitate manipulation thereof.

3. A surgical instrument as recited in claim 1, wherein the latch is connected with the body at a pivot point such that the latch is rotatable about the pivot point.

4. A surgical instrument as recited in claim 1, wherein the latch defines a slot configured for disposal of the proximal end of the first member.

5. A surgical instrument as recited in claim 4, wherein the slot defines a first movable limit and a second movable limit for the proximal end of the first member.

6. A surgical instrument as recited in claim 1, wherein the latch is biased outwardly from the body to the non-locking orientation.

7. A surgical instrument as recited in claim 1, wherein the latch is manipulable from the non-locking orientation to translate the first member relative to the second member.

8. A surgical instrument as recited in claim 1, wherein the lock is resiliently biased to a locking orientation to prevent movement of the latch.

9. A surgical instrument as recited in claim 1, wherein the lock is movable between a locking orientation to prevent movement of the latch and a non-locking orientation such that the latch is movable relative to the body.

10. A surgical instrument as recited in claim 1, wherein the third member is angled between 10 and 80 degrees relative to the first and second members such that in the locking orientation, the third member is substantially non-parallel and non-perpendicular with an extender.

11. A surgical instrument as recited in claim 1, wherein the third member is manipulable such that a force oriented in a first direction is applied to the third member and a force oriented in a second opposing direction is applied to the third member to release the latch.

12. A surgical instrument as recited in claim 1, wherein the lock defines an inclined ramp engageable with the latch to facilitate movement of the latch from the locking orientation to the non-locking orientation.

13. A surgical instrument as recited in claim 1, further comprising a part that engages the second member, the part being rotatably coupled to the body and configured to translate the second member relative to the body upon rotation of the part relative to the body.

14. A surgical implant system comprising:
a surgical instrument comprising:
    a body;
    a first member extending between a proximal end and a distal end comprising a first jaw;
    a second member extending between a proximal end connected with the body and a distal end comprising a second jaw; and
    a third member connected to the proximal end of the first member and the body to axially translate the first jaw relative to the second jaw, the third member including a latch and a lock engageable with the latch;
a spinal rod,
wherein the latch is disposable in a locking orientation such that inner surfaces of the jaws engage the spinal rod and rotatable to a non-locking orientation such that the lock disengages the latch and the latch is biased relative to the body such that the jaws are disposed to disengage the spinal rod, the first jaw being distal to the second jaw when the latch is in the non-locking orientation and the locking orientation; and
    an extender including a first wall and a second wall, the walls defining an implant cavity therebetween, the implant cavity defining a first width dimension between the walls.

15. A surgical implant system as recited in claim 14, wherein the distal end of the second member includes a second width dimension greater than the first width dimension to prevent disposal of the distal end of the second member within the implant cavity.

16. A surgical instrument as recited in claim 14, wherein the lock is movable between a locking orientation to prevent movement of the latch and a non-locking orientation such that the latch is movable relative to the body.

17. A surgical implant system as recited in claim 14, wherein the second member defines a longitudinal axis, the inner surfaces being spaced apart a first distance along the longitudinal axis when the latch is in the locking orientation and a second distance along the longitudinal axis when the latch is in the non-locking orientation, the second distance being greater than the first distance.

18. A surgical instrument comprising:
a body;
a first member extending between a first end and a second end;
a second member extending between a first end connected with the body and a second end; and
a third member connected to the first end of the first member and the body to relatively axially translate the second ends, the third member including a latch and a lock engageable with the latch, the latch comprising a slot having a first movable limit and a second movable limit,
wherein the latch is disposable in a locking orientation such that the second ends engage a spinal construct and rotatable to a non-locking orientation such that the lock disengages the latch and the latch is biased relative to the body such that the second ends are disposed to disengage the spinal construct, and
wherein the first end of the first member comprises a bead positioned in the slot, the bead moving from the first movable limit to the second movable limit as the latch moves from the non-locking orientation to the locking orientation.

19. A surgical instrument as recited in claim 18, wherein the bead is positioned adjacent to the fist movable limit when the latch is in the non-locking orientation and the bead is positioned adjacent to the second movable limit when the latch is in the locking orientation.

20. A surgical instrument as recited in claim 18, wherein the second end of the first member comprises a first jaw and the second end of the second member comprises a second jaw, the first jaw being distal to the second jaw when the latch is in the non-locking orientation and the locking orientation.

* * * * *

UNITED STATES PATENT AND TRADEMARK OFFICE
CERTIFICATE OF CORRECTION

| | | |
|---|---|---|
| PATENT NO. | : 9,554,835 B2 | Page 1 of 1 |
| APPLICATION NO. | : 13/827485 | |
| DATED | : January 31, 2017 | |
| INVENTOR(S) | : Brinkman et al. | |

It is certified that error appears in the above-identified patent and that said Letters Patent is hereby corrected as shown below:

On the Title Page

On Page 2, in item (56), under "U.S. PATENT DOCUMENTS", in Column 1, Line 21, delete "Justis et al." and insert -- Justis --, therefor.

On Page 2, in item (56), under "U.S. PATENT DOCUMENTS", in Column 2, Line 12, delete "McLean" and insert -- McLean et al. --, therefor.

In the Specification

In Column 13, Line 46, delete "Dekutowski" and insert -- Dekutoski --, therefor.

In the Claims

In Column 18, Line 12, in Claim 16, delete "surgical instrument" and insert -- surgical implant system --, therefor.

In Column 18, Line 47, in Claim 19, delete "fist" and insert -- first --, therefor.

Signed and Sealed this
Second Day of May, 2017

Michelle K. Lee
*Director of the United States Patent and Trademark Office*